US010321943B1

(12) United States Patent
Guthlein

(10) Patent No.: US 10,321,943 B1
(45) Date of Patent: Jun. 18, 2019

(54) INTERNAL FIXATION DEVICE

(71) Applicant: James Guthlein, Wayne, PA (US)

(72) Inventor: James Guthlein, Wayne, PA (US)

( * ) Notice: Subject to any disclaimer, the term of this patent is extended or adjusted under 35 U.S.C. 154(b) by 71 days.

(21) Appl. No.: 15/442,723

(22) Filed: Feb. 27, 2017

Related U.S. Application Data

(63) Continuation-in-part of application No. 13/756,600, filed on Feb. 1, 2013, now Pat. No. 9,579,133.

(51) Int. Cl.
*A61B 17/80* (2006.01)
*A61B 17/00* (2006.01)

(52) U.S. Cl.
CPC .......... *A61B 17/80* (2013.01); *A61B 17/8057* (2013.01); *A61B 2017/00004* (2013.01); *A61B 2017/00893* (2013.01)

(58) Field of Classification Search
CPC .................. A61B 17/8085; A61B 17/8028
See application file for complete search history.

(56) References Cited

U.S. PATENT DOCUMENTS

2009/0299369 A1* 12/2009 Orbay .................... A61B 17/80
606/70
2010/0305569 A1* 12/2010 Leuenberger ...... A61B 17/8023
606/70

* cited by examiner

*Primary Examiner* — Olivia C Chang
(74) *Attorney, Agent, or Firm* — Joseph E. Maenner; Maenner & Associates, LLC

(57) ABSTRACT

A medical implant according to the present invention includes a substrate having a plurality of discrete connection portions. Each connection portion has a top surface, a bottom surface, and a through-opening extending between the top surface and the bottom surface. A connecting member extends between each connection portion and connects adjacent connecting portions to each other. At least one of the plurality of connection portions has a first width and at least one of the connecting members has a second width, different from the first width. An outer covering substantially encompasses the substrate. The outer covering extends around the through-openings and encompasses the connecting member.

18 Claims, 39 Drawing Sheets

INTERNAL FIXATION DEVICE

CROSS-REFERENCE TO RELATED APPLICATION

The present application is a Continuation-in-Part of U.S. Pat. No. 9,579,133, issued on Feb. 28, 2017, which is incorporated by reference herein in its entirety.

FIELD OF THE INVENTION

The present invention relates to a device to be used in the field of surgical implantation for use in long bones, craniomaxiofacial, and spinal areas of the human body where internal fixation is needed. The invention is applicable to a wide range of surgical approaches not limited to reconstruction, trauma, deformity correction, and cosmetic surgeries.

BACKGROUND OF THE INVENTION

Internal fixation devices have been in existence from the earlier part of the 20th century, gaining further credibility in the medical community in the later half of the century. Internal fixation relies on four principles: preservation of the blood supply; anatomic reduction; stable fixation; and early and functional movement of the operative area. Devices used in this practice predominantly consist of metallic implants made from implant grade stainless steel, commercially pure grades of titanium and titanium alloys. In the practice of internal fixation there are three main branches, namely trauma, craniomaxiofacial, and spine. In Trauma, internal fixators fall into two categories of use, intermedullary nails, which are rods inserted into long bones thus securing the bone internally within itself; and secondly with what are known as plates and screws. Plates and screws can be found in all three branches of internal fixation. Plates in most cases must be used with screws, however screws do not have to be used with plates.

While these advancements in plate and screw technology, along with a deeper understanding of less invasive surgical techniques, have provided surgeons to deliver improved patient outcomes, there still exists a need to improve these internal fixation devices.

BRIEF SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Briefly, the present invention discloses a medical implant including a substrate having a plurality of discrete connection portions. Each connection portion has a top surface, a bottom surface, and a through-opening extending between the top surface and the bottom surface. A connecting member extends between each connection portion and connects adjacent connecting portions to each other. At least one of the plurality of connection portions has a first width and at least one of the connecting members has a second width, different from the first width. An outer covering substantially encompasses the substrate. The outer covering extends around the through-openings and encompasses the connecting member.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
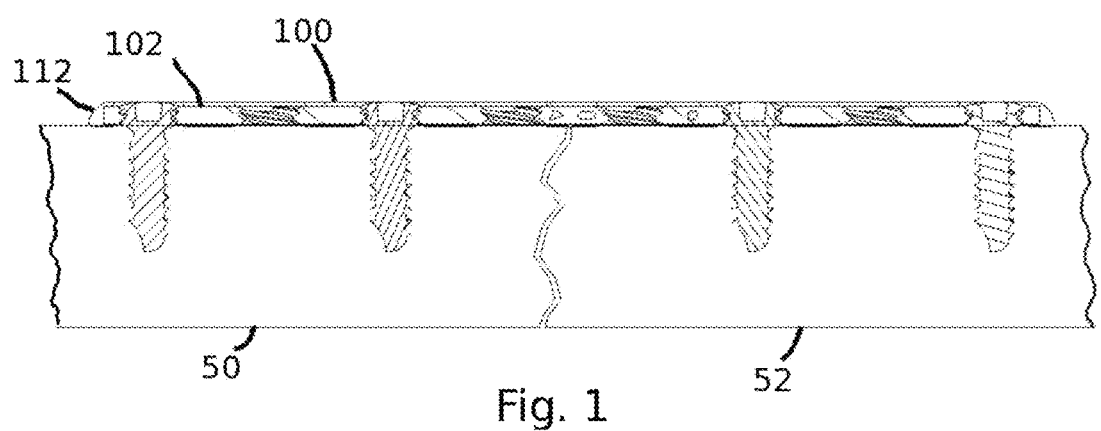
FIG. 1 is a side elevational view of an internal fixation implant according to a first exemplary embodiment of the present invention, coupling to pieces of broken bone together.

In the drawings, like numerals indicate like elements throughout. Certain terminology is used herein for convenience only and is not to be taken as a limitation on the present invention. The terms "proximal" and "distal" refer, respectively, to directions toward and away from a body. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Referring now to FIG. 1, a medical implant 100 according to a first exemplary embodiment of the present invention is used to internally fixate broken pieces 50, 52 of bone after pieces 50, 52 are set. Implant 100 is envisioned to be a temporary internal fixation device and may be removed after pieces 50, 52 fuse together, although those skilled in the art will recognize that implant 100 may permanently remain after pieces 50, 52 fuse together.

Figure 2:
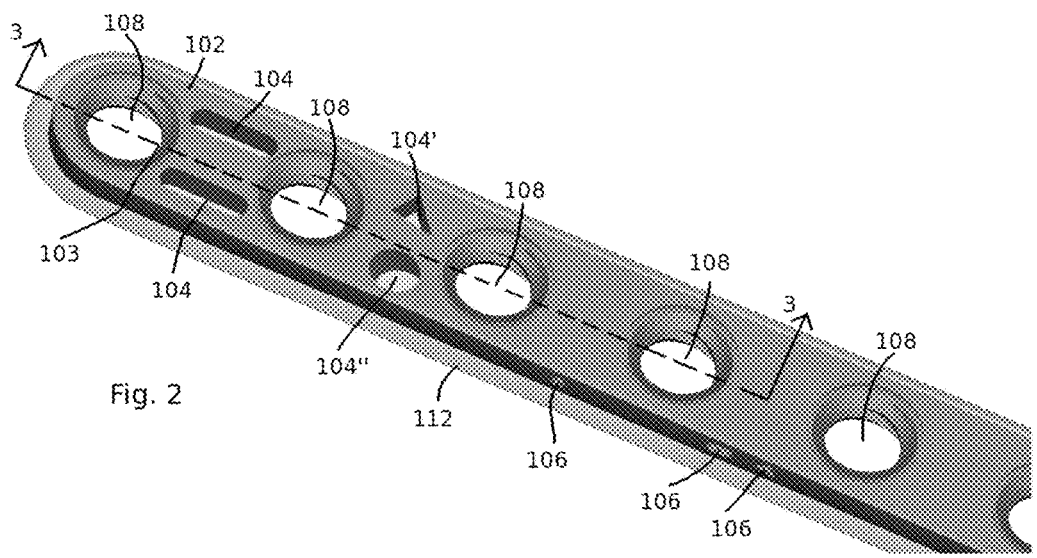
FIG. 2 is a perspective view of the internal fixation implant shown in FIG. 1.
Figure 3:
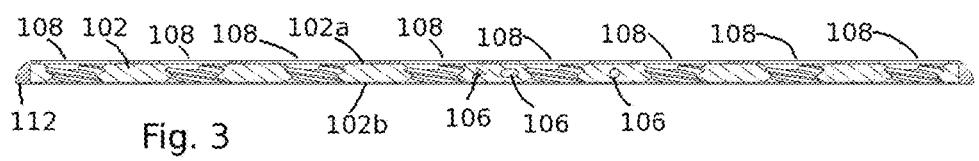
FIG. 3 is a sectional view of the internal fixation implant shown in FIG. 2, taken along lines 3-3.

Referring to FIGS. 2 and 3, medical implant 100 includes a substrate 102 and an outer covering 112 substantially encompassing substrate 102. Substrate 102 has a longitudinal axis 103 that extends therethrough. Substrate 102 includes an upper surface 102a and a lower surface 102b. Substrate 102 further includes a first plurality of openings 104, 106 and a second plurality of openings 108 formed therein. All of openings 104, 106, 108 may be chamfered at each of upper surface 102a and lower surface 102b (as shown in FIG. 5A) or, alternatively, only at an upper surface 102a (as shown in FIG. 6).

Substrate 102 may be constructed from a rigid material. While an exemplary rigid material may be one selected from the group consisting of a metal, a ceramic, and a composite material, those skilled in the art will recognize that other rigid, biocompatible and/or combinations of materials may be used.

Figure 4:
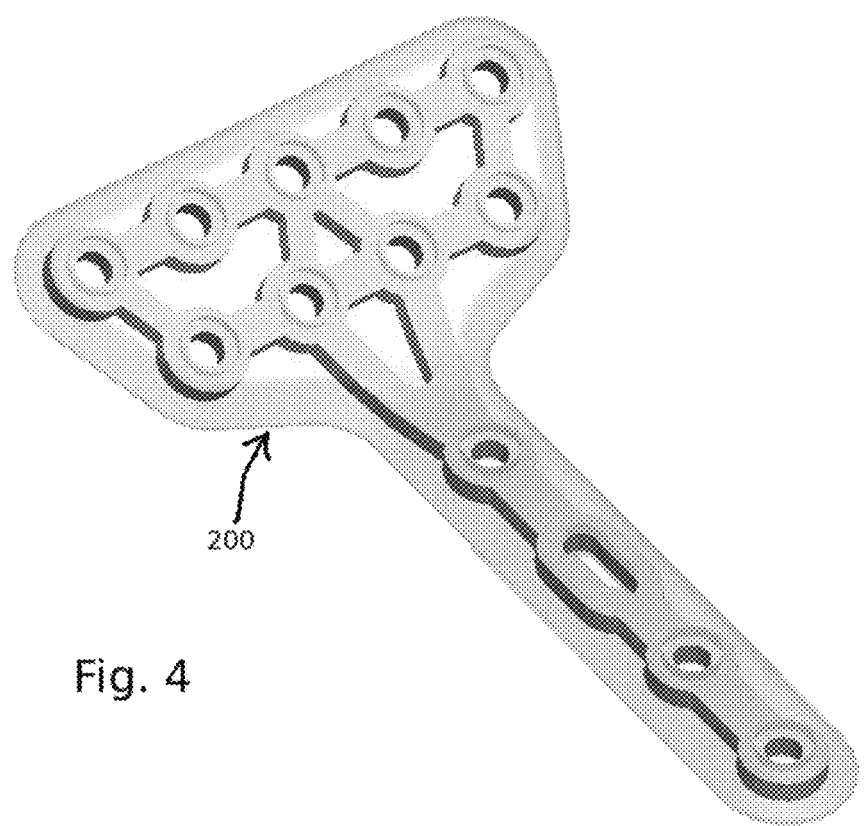
FIG. 4 is a perspective view of an internal fixation implant according to a second exemplary embodiment of the present invention.

Further, while implant 100 shown in FIGS. 2 and 3 is an elongated rod or bar and may be used to secure two elongated bone pieces 50, 52 (as shown in FIG. 1), such as a proximal end and a distal end of a tibia bone together, other implant shapes, such as implant 200, shown in FIG. 4, which is a generally "T-shaped" implant used for a distal radius (wrist) are also within the scope and intent of the present invention. Further, while substrate 102 is shown as a bar with a uniform cross-section, those skilled in the art will recognize that substrate 102 may have a non-uniform cross-section (shown in FIG. 5) as well.

Some of the first plurality of openings 104 extend through substrate 102 and allow outer covering 112 to extend therethrough to securely bind outer covering 112 to substrate 102. While openings 104 extend generally orthogonally to longitudinal axis 103, openings 104' and 104" may be formed at compound angles that extend obliquely relative to longitudinal axis 103. Others 106 of the first plurality of openings 104 may extend partially or entirely through substrate 102. Outer covering 112 extends into this plurality of openings 106 to further secure outer covering 112 to substrate 102. Similar to openings 104' and 104", at least some of openings 106 may be formed at compound angles that extend obliquely relative to longitudinal axis 103.

Second plurality of openings 108 extends through substrate 102 and is used to allow a fastener 120 (shown FIG. 6) to extend therethrough to secure substrate 102 to either piece 50, 52 of bone. In the event that fastener 120 is a screw, some of second plurality of openings 108 may include threads 109 (shown FIG. 6) into which fastener 120 is screwed.

Figure 5:
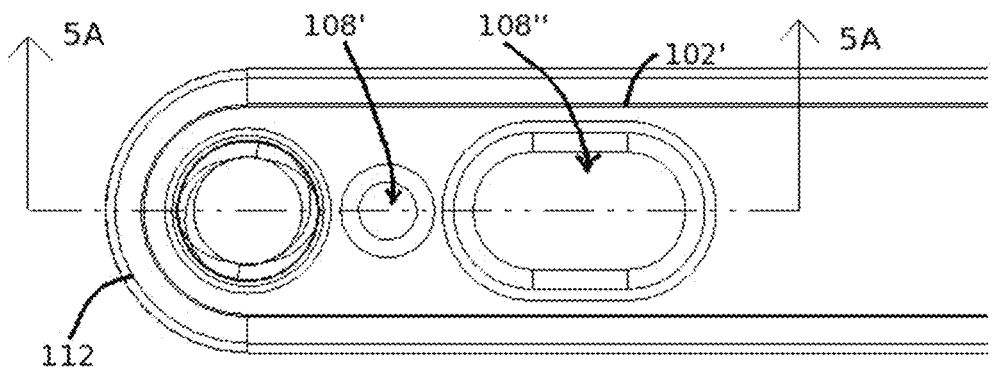
FIG. 5 is a top plan view of an alternative embodiment of an internal fixation implant according to the present invention.
Figure 5A:
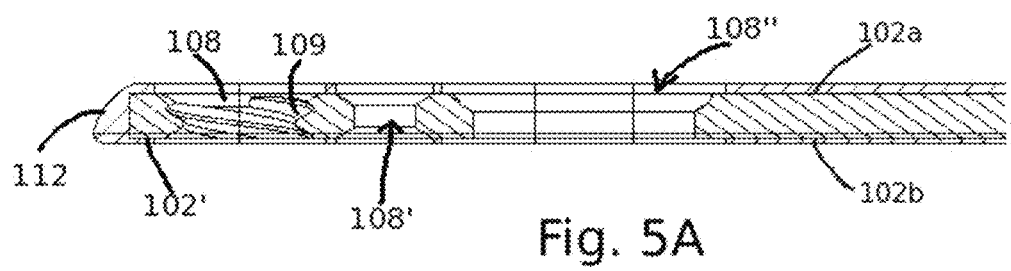
FIG. 5A is a sectional view of the internal fixation implant shown in FIG. 5, taken along lines 5A-5A of FIG. 5.
Figure 6:
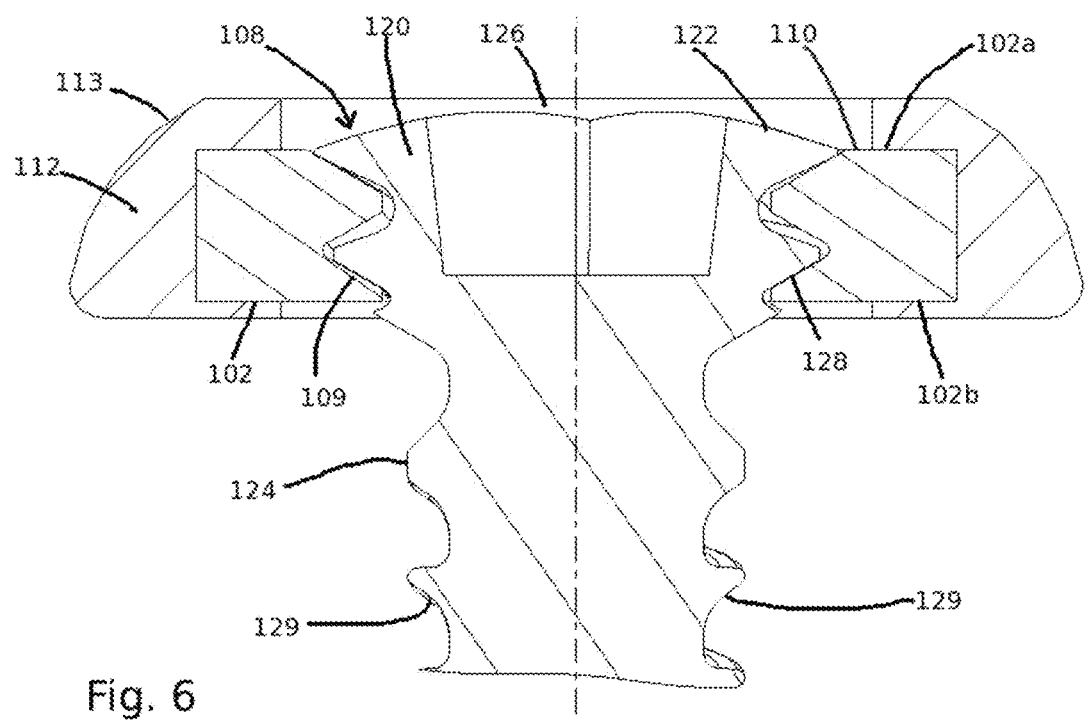
FIG. 6 is a side view, in section, of a fastener extending through internal fixation implant FIG. 1.

Alternatively, as shown in FIGS. 5 and 5A, with a substrate 102', others of second plurality of openings 108' may be unthreaded and are used to accept K-wires or other provisional fixation devices (not shown). Second plurality of openings 108, 108' may be generally circular. Alternatively, others of second plurality of openings 108" may be elongated slots that allow fastener 122 be inserted thereinto to allow adjustment of implant 100 along the length of pieces 50, 52 of bone.

Referring now to FIG. 6, fastener 120 may be a screw or other suitable fastening device. Additionally, fastener 120 may be constructed from stainless steel, titanium or other suitable, biocompatible material.

Fastener 120 includes a screw head 122 and an elongated screw shaft 124. Screw head 122 may include an opening 126 that is sized and shaped to receive a torquing device, such as, for example a screwdriver (not shown) or other type of driver. Screw head 122 may be tapered or chamfered, such that a portion of screw head 122 proximate to opening 126 is higher than the outer edge of head 122. Screw head 122 may also include threads 128 that are sized to engage mating threads 109 in opening 108.

Screw shaft 124 has an outer diameter that is smaller than the diameter of opening 108 so that screw shaft 124 can be inserted through opening 108. Additionally, screw shaft 124 may also be threaded with threads 129 that are used to grip a safe bone (not shown) so that fastener 120 secures implant 100 to the bone.

Outer covering 112 substantially encompasses substrate 102 and has an absence of sharp exterior edges. As shown FIG. 6, exterior edge 113 of outer covering 112 is generally chamfered and curved to eliminate any sharp edges.

As described above, outer covering 112 extends into first plurality of openings 104, 106, but not into second plurality of openings 108. Outer covering 112 extends around second plurality of openings 108 such that a portion of substrate 102 surrounding each of second plurality of openings 108 is not encompassed by outer covering 112. As shown FIG. 6, an uncovered portion 110 of substrate 102 around second opening 108 allows the head 122 of fastener 120 to directly engage substrate 102.

Outer covering 112 may be sufficiently thick over the top surface of substrate 102 such that, when fastener 120 is inserted through substrate 102, outer covering extends above screw head 122 such the screw head 122 extends between substrate 102 and the exterior surface of outer covering 112. Those skilled in the art, however, will recognize that screw head 122 may extend above the exterior surface of outer covering 112.

As shown FIG. 6, where outer covering 112 does not extend over substrate 102, outer covering 112 extends generally orthogonally to upper surface 102a and lower surface 102b. Those skilled in the art, however, will recognize that outer covering 112 can taper toward upper surface 102a and lower surface 102b to provide a smooth transition between outer covering 112 and substrate 102.

In an exemplary embodiment, outer covering 112 is constructed from an elastomer, such as, for example a silicone elastomer, a thermoset elastomer, a thermoplastic elastomer, or other biocompatible material.

Implant 100 can be manufactured, in the case of an elastomer, by taking substrate 102, masking the plurality of holes 104, 106, and inserting substrate 102 into a compression mold cavity in a compression machine (not shown) in conjunction with a slug of the elastomeric material. The compression mold cavity is in the final shape of outer covering 112. Once the compression machine is activated, applying compression to elastomeric slug, compressive forces will cause the elastomer to cover substrate 102, forming outer covering 112, wherefrom the masking can be removed from the plurality of openings in substrate 102.

Figure 7:
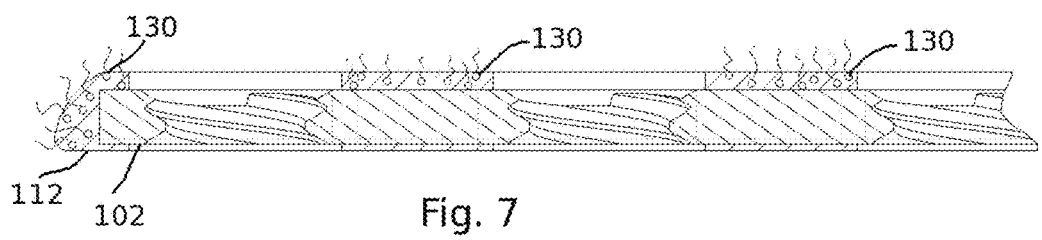
FIG. 7 is a side view, in section, of an alternative embodiment of the present invention.

In an exemplary embodiment, as shown FIG. 7, outer covering 112 is infused with a medicament 130. Medicament 130 may be an antimicrobial medicament to reduce the likelihood of infection. After implant 100 is inserted into the patient, medicament 130 exudes from outer covering 112 and is absorbed by the patient.

Figure 8:
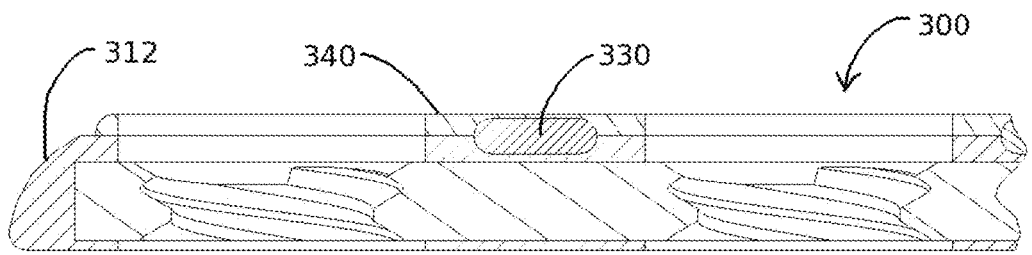
FIG. 8 is a side view, in section, of another alternative embodiment of the present invention.

In an alternative embodiment, shown FIG. 8, a medical implant 300, similar to medical implant 100 described above, includes a coating 340 disposed over outer covering 312. A medicament 330 is disposed between coating 340 and outer covering 312. Coating 340 may be constructed from hydroxyapatite, poly (L-lactides) or other suitable biodegradable material. Coating 340 is biodegradable such that coating 340 dissolves after implant 300 is inserted into the patient. Medicament 330 is then released from implant 300 and is absorbed by the patient. In order to prevent implant 300 from listening with respect to bone pieces 50, 52 (not shown in FIG. 8) as coating 340 dissolves, coating 340 is not applied to the bottom portion of implant 300 where implant 300 engages bone pieces 50, 52.

Further, the present invention includes a kit that includes implant 100, 200, or 300 as well as at least one, and preferably a plurality of, fasteners 120. Fasteners 120 are used to secure implant to both broken bone pieces 50, 52. The kit can also include temporary fixation devices, such as, for example K-wires (not shown), torquing devices (not shown), and/or other materials necessary for the proper insertion of implant 100, 200, 300 into a patient.

Referring now to FIGS. 9-15, a medical implant 400 according to an alternative exemplary embodiment of the present invention is shown. Implant 400 includes a substrate 402 having a superior surface 404, an opposing inferior surface 406, and a central portion 408 between and connecting superior surface 404 and inferior surface 406.

Substrate 402 also includes plurality of discrete connection portions 409 that each has an inwardly tapered top surface 410 at superior surface 404, a bottom surface 412 at inferior surface 406, and a through-opening 413 extending between top surface 410 and bottom surface 412. Each through-opening 413 is sized to allow a connection member, such as a screw (not shown) to be inserted therethrough to secure implant 400 to a structure, such as bone.

Through-opening 413, along with other through-openings identified as element X13 or XX13, wherein "X" is a whole number 5 through 9, and "XX" is a whole number 10 through 13, can be threaded to threadingly engage a screw. Alternatively, through-opening 413 can be smooth bore, without any threads.

Figure 12:
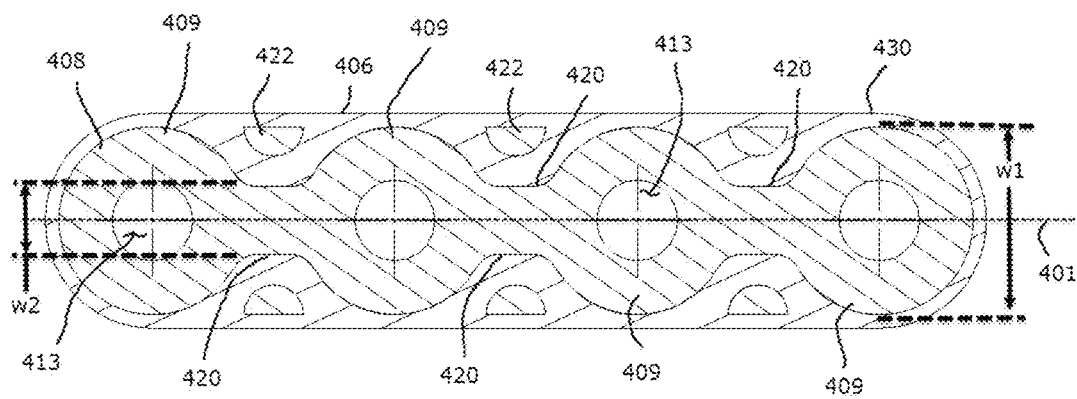
FIG. 12 is a top planar view, in section, of the implant of FIG. 11, taken along lines 12-12 of FIG. 11.
Figure 13:
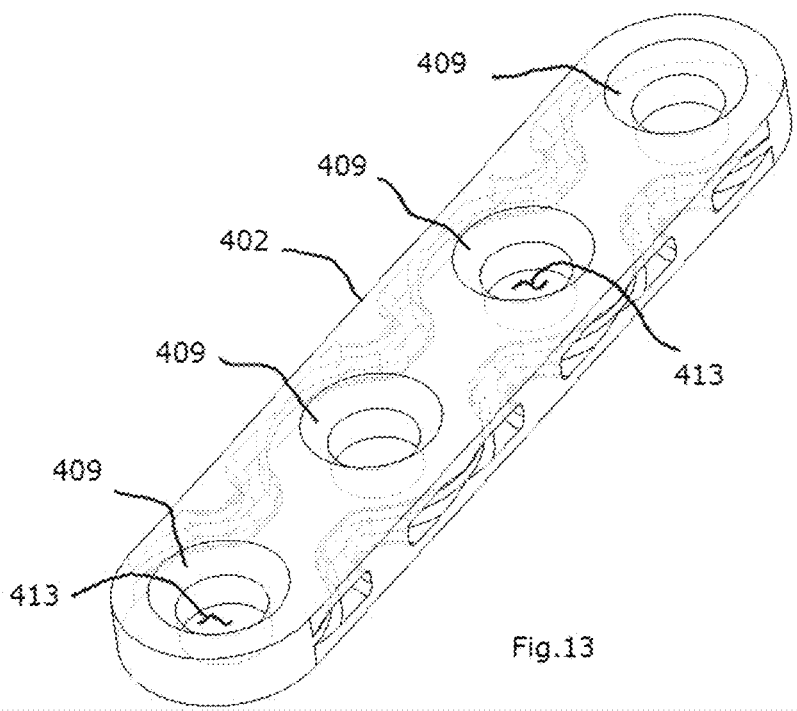
FIG. 13 is a perspective view of a substrate of the implant of FIG. 9.
Figure 14:
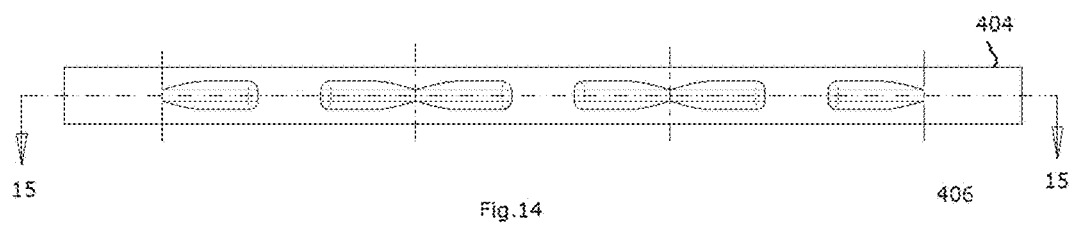
FIG. 14 is a side elevational view of the substrate of FIG. 13.

A connecting member 420 extends between each connection portion 409 and connects adjacent connection portions 409 to each other. As shown in FIG. 12, along central portion 408, connection portions 409 can have a generally annular shape, while connecting members 420 are generally elongate and extend along a central longitudinal axis 401. Connection portions 409 have a first width W1 and connecting members 420 have a second width W2, different from first width W1. In an exemplary embodiment, second width W2 is smaller than first width W1.

Figure 15:
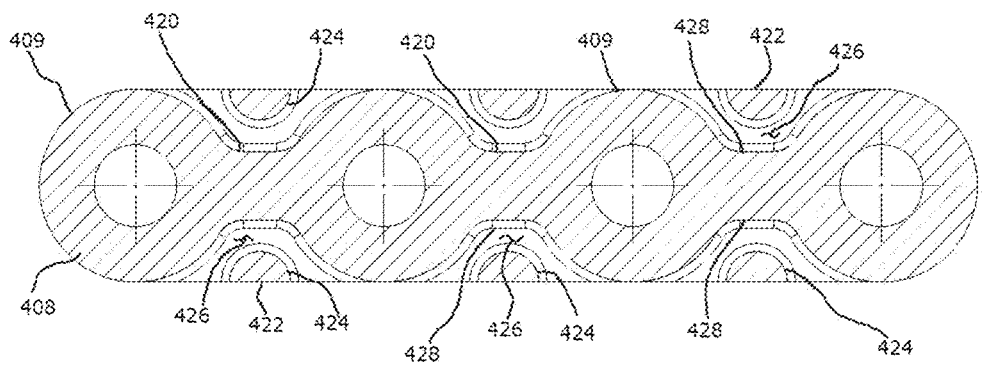
FIG. 15 is a top planar view, in section, of the substrate of FIG. 14, taken along lines 15-15 of FIG. 14.
Figure 16:
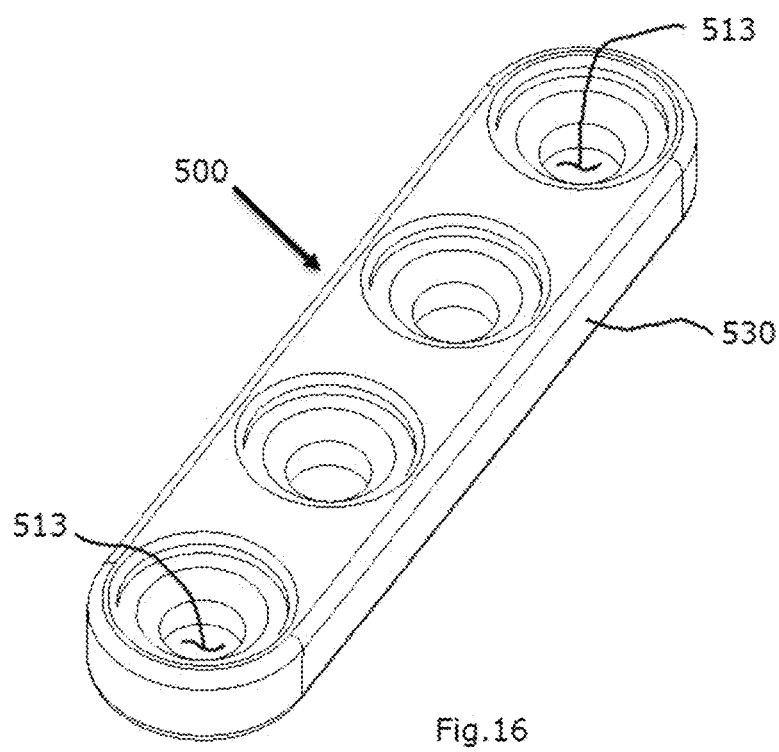
FIG. 16 is a perspective view of another alternative embodiment of an internal fixation implant of the present invention.
Figure 17:
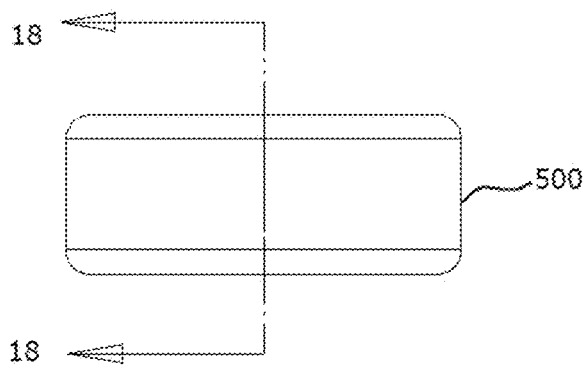
FIG. 17 is an end elevational view of the implant shown in FIG. 16.
Figure 18:
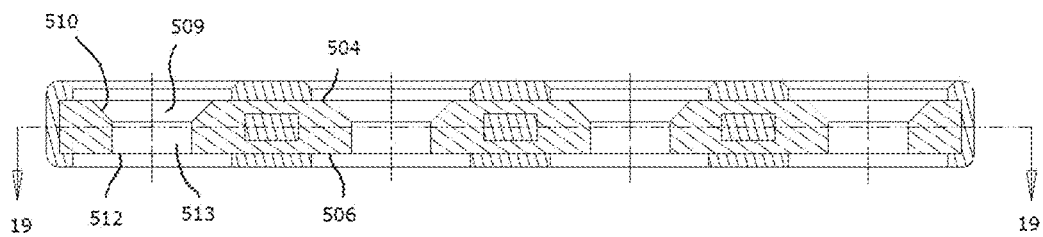
FIG. 18 is a sectional view of the implant of FIG. 17, taken along lines 18-18 of FIG. 17.
Figure 19:
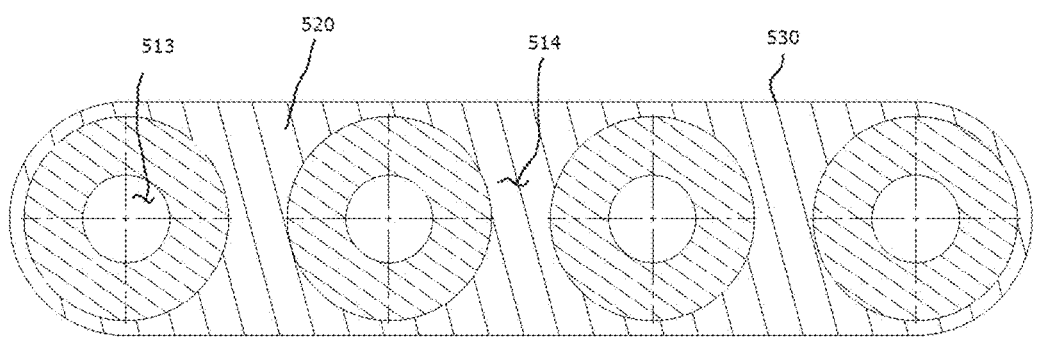
FIG. 19 is a top planar view, in section, of the implant of FIG. 18, taken along lines 19-19 of FIG. 18.
Figure 20:
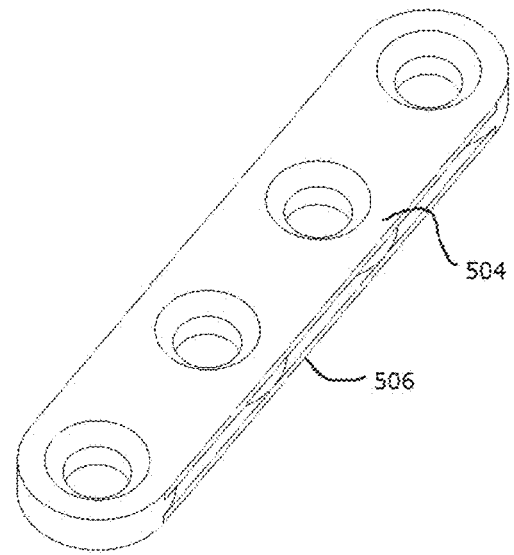
FIG. 20 is a perspective view of a substrate of the implant of FIG. 16.
Figure 21:
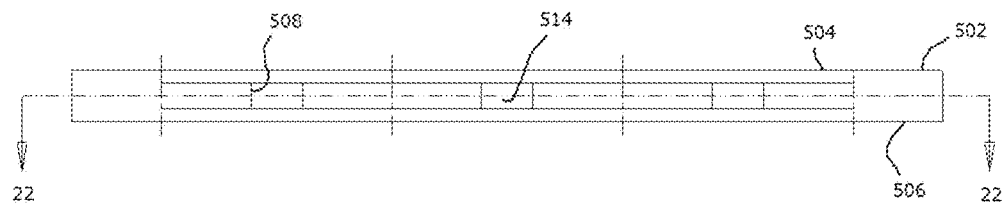
FIG. 21 is a side elevational view of the substrate of FIG. 20.

As further shown in FIG. 15, central portion 408 includes posts 422 that are laterally aligned with, but separate from, connecting members 420, and extend between superior surface 404 and inferior surface 406. Each post 422 forms a first wall 424 of a channel 426 that uses adjacent connection portions 409 and an intervening connecting member 420 to form a second wall 428.

Figure 9:
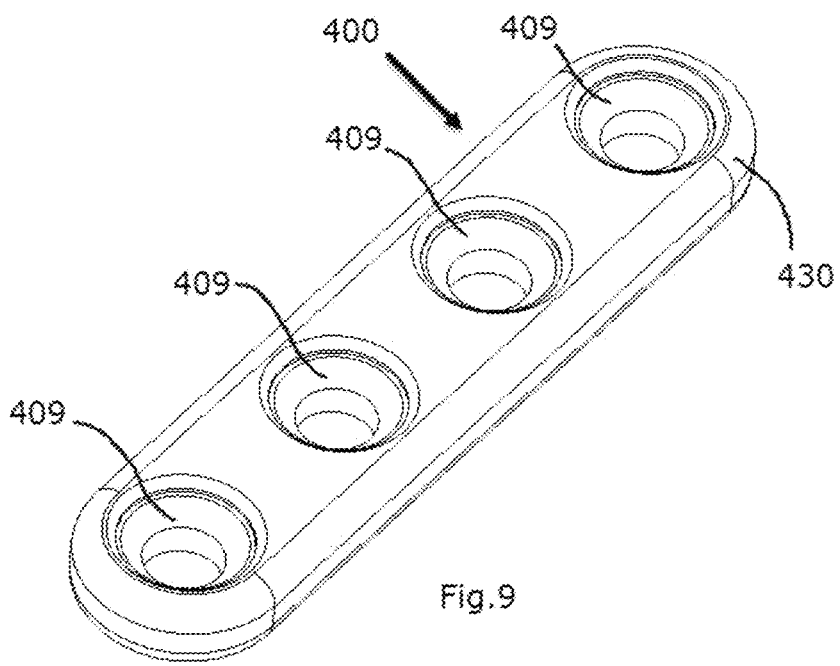
FIG. 9 is a perspective view of another alternative embodiment of an internal fixation implant of the present invention.
Figure 10:
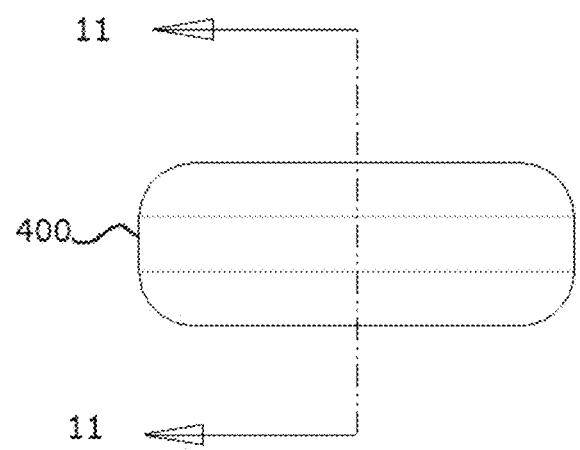
FIG. 10 is an end elevational view of the implant shown in FIG. 9.
Figure 11:
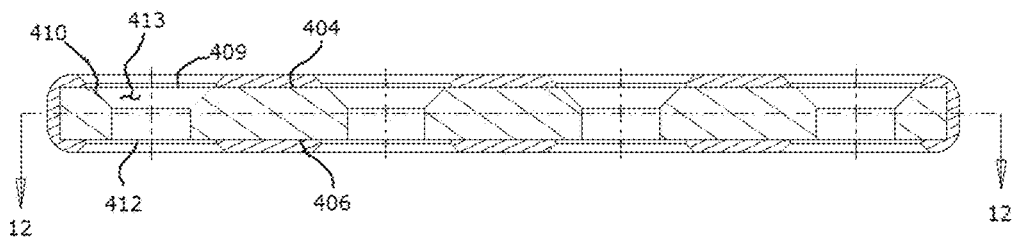
FIG. 11 is a sectional view of the implant of FIG. 10, taken along lines 11-11 of FIG. 10.

Referring to FIGS. 9 and 12, an outer covering 430 substantially encompasses substrate 402. Outer covering 430 extends around through-openings 413 and encompasses connecting member 420. Outer covering 430 also extends into each channel 426. By extending into channels 426, outer covering 430 is securely affixed to substrate 402 without having to cross central longitudinal axis 401 between superior surface 404 and inferior surface 406.

Referring now to FIGS. 16-22, a medical implant 500 according to an alternative exemplary embodiment of the present invention is shown. Implant 500 includes a substrate 502 having a superior surface 504, an opposing inferior surface 506, and a central portion 508 between and connecting superior surface 504 and inferior surface 506.

Substrate 502 also includes plurality of discrete connection portions 509 that each has an inwardly tapered top surface 510 at superior surface 504, a bottom surface 512 at inferior surface 506, and a through-opening 513 extending between top surface 510 and bottom surface 512. Each through-opening 513 is sized to allow a connection member, such as a screw (not shown) to be inserted therethrough to secure implant 500 to a structure, such as bone.

Figure 22:
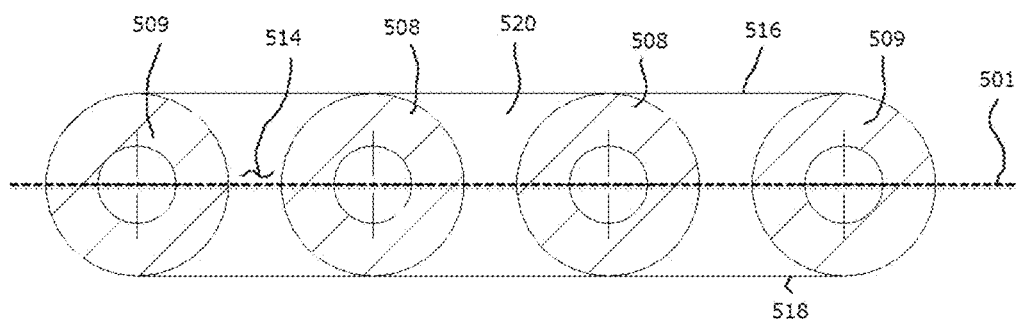
FIG. 22 is a top planar view, in section, of the substrate of FIG. 21, taken along lines 22-22 of FIG. 21.
Figure 23:
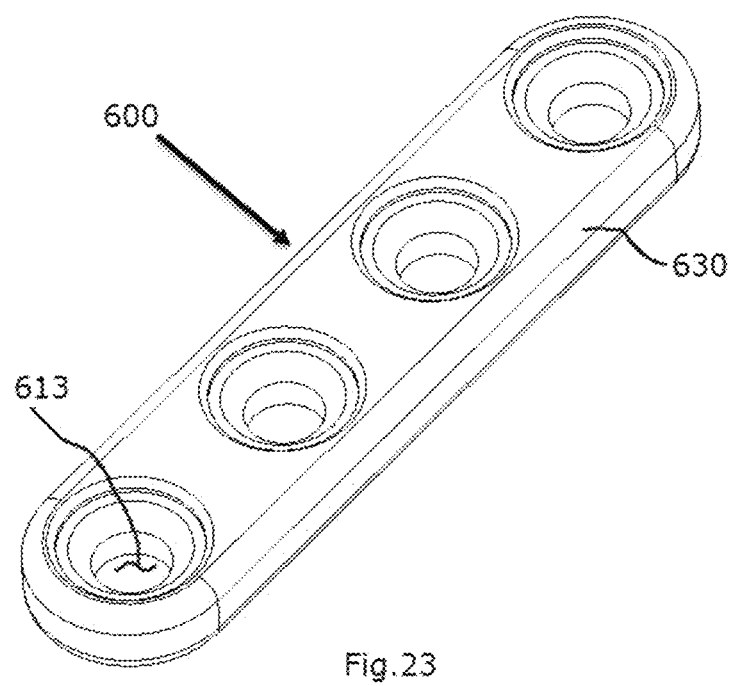
FIG. 23 is a perspective view of another alternative embodiment of an internal fixation implant of the present invention.
Figure 24:
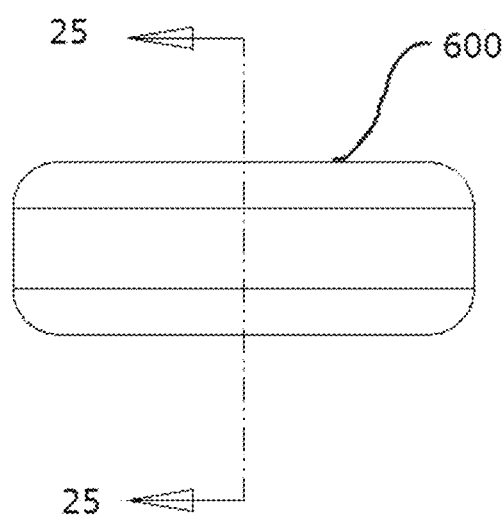
FIG. 24 is an end elevational view of the implant shown in FIG. 23.
Figure 25:
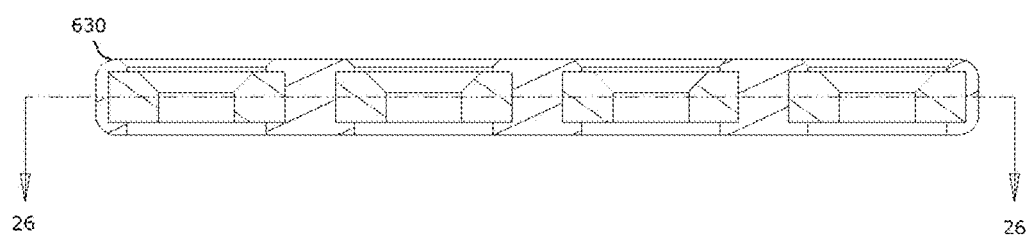
FIG. 25 is a sectional view of the implant of FIG. 24, taken along lines 25-25 of FIG. 24.
Figure 26:
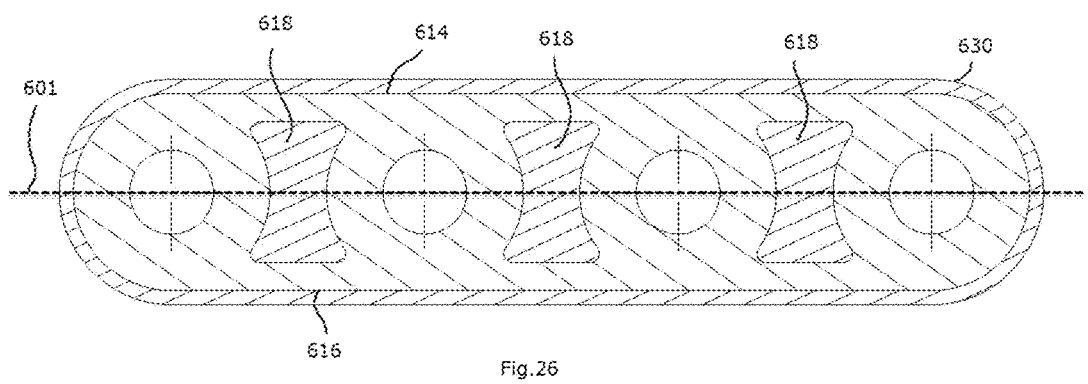
FIG. 26 is a top planar view, in section, of the implant of FIG. 25, taken along lines 26-26 of FIG. 25.
Figure 27:
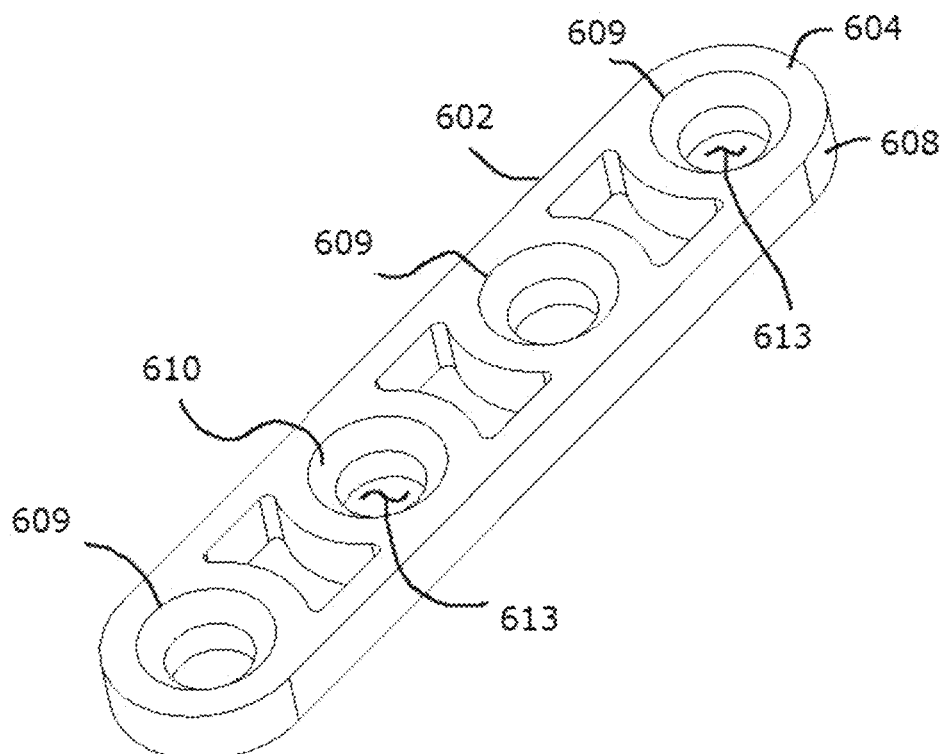
FIG. 27 is a perspective view of a substrate of the implant of FIG. 23.
Figure 28:
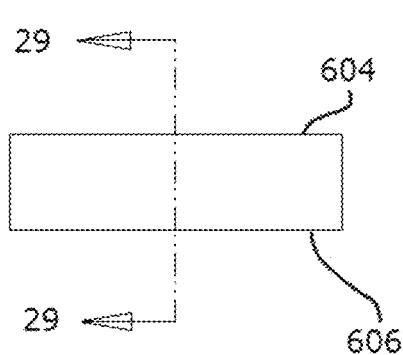
FIG. 28 is an end elevational view of the substrate in FIG. 27.
Figure 29:
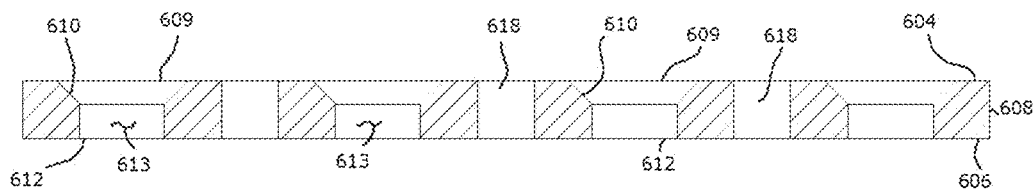
FIG. 29 is a side elevational view of the substrate of FIG. 28, in section, taken along lines 29-29 of FIG. 28.

A connecting member 520 extends between each connection portion 509 along superior surface 504 and inferior surface 506 and connects adjacent connection portions 509 to each other. As shown in FIG. 22, along central portion 508, connection portion 509 is not present, resulting in a passage 514 extending across a central longitudinal axis 501 from one longitudinal side 516 of substrate 402 to an opposing longitudinal side 518 of substrate 502.

An outer covering 530 substantially encompasses substrate 502. Outer covering 530 extends around through-openings 513 and encompasses connecting member 520. Outer covering 530 also extends into each passage 514. By extending into passages 514, outer covering 530 is securely affixed to substrate 502 by crossing central longitudinal axis 501 between superior surface 504 and inferior surface 506.

Referring now to FIGS. 23-30, a medical implant 600 according to an alternative exemplary embodiment of the present invention is shown. Implant 600 includes a substrate 602 having a superior surface 604, an opposing inferior surface 606, and a central portion 608 between and connecting superior surface 604 and inferior surface 606.

Substrate 602 also includes plurality of discrete connection portions 609 that each has an inwardly tapered top surface 610 at superior surface 604, a bottom surface 612 at inferior surface 606, and a through-opening 613 extending between top surface 610 and bottom surface 612. Each through-opening 613 is sized to allow a connection member, such as a screw (not shown) to be inserted therethrough to secure implant 600 to a structure, such as bone.

Figure 30:
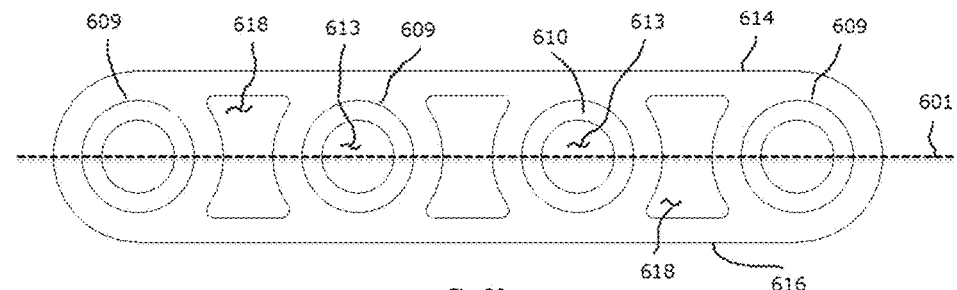
FIG. 30 is a top planar view, of the substrate of FIG. 29.
Figure 31:
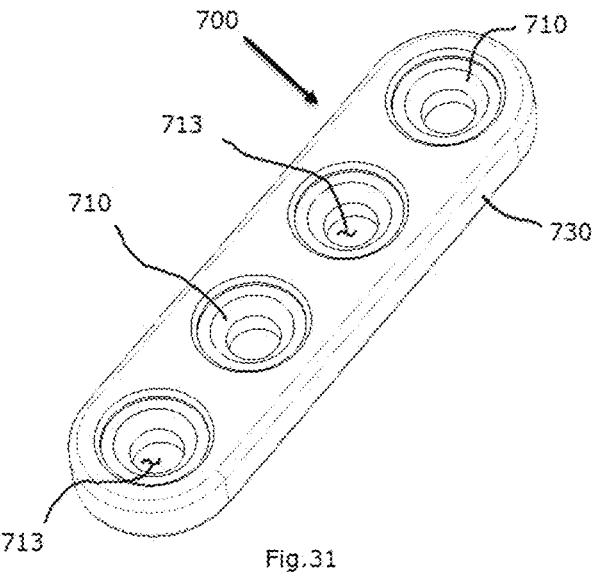
FIG. 31 is a perspective view of another alternative embodiment of an internal fixation implant of the present invention.
Figure 32:
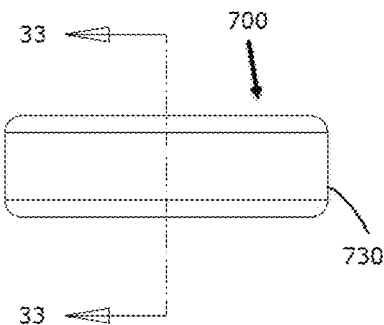
FIG. 32 is an end elevational view of the implant shown in FIG. 31.
Figure 33:
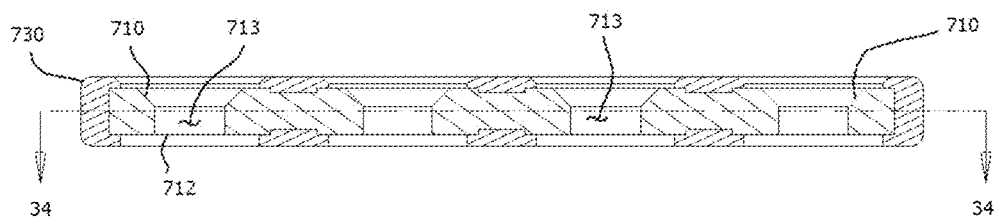
FIG. 33 is a side elevational view of the implant of FIG. 31, in section, taken along lines 33-33 of FIG. 32.
Figure 34:
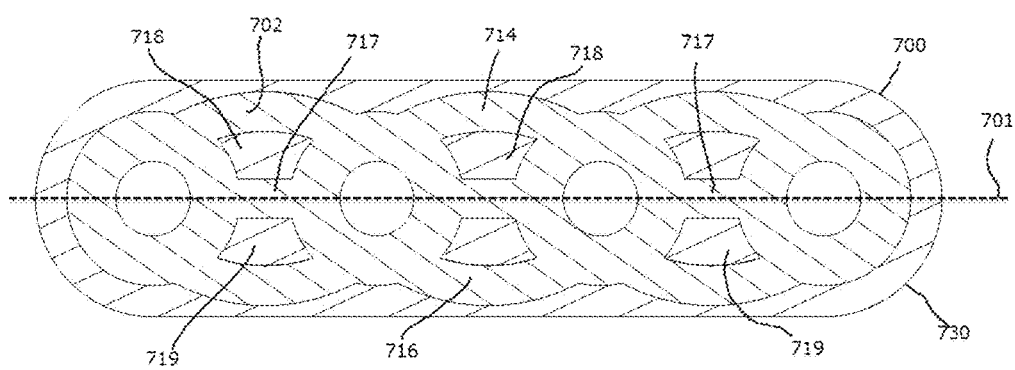
FIG. 34 is a top planar view, in section, of the substrate of FIG. 33, taken along lines 34-34 of FIG. 33.
Figure 35:
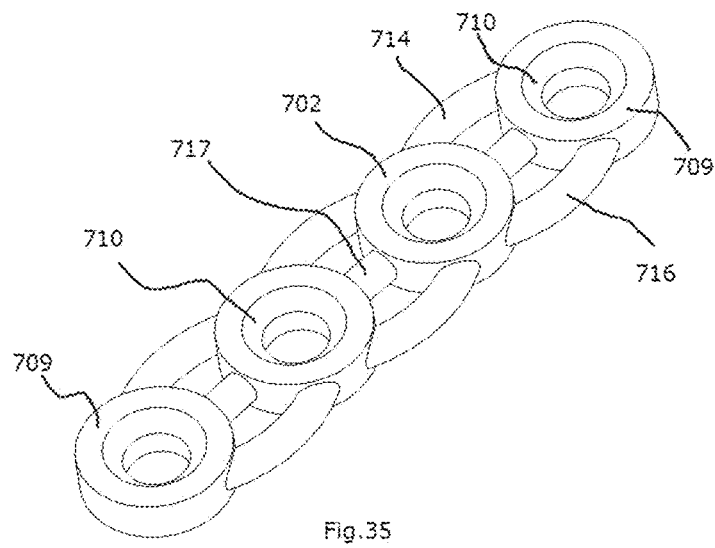
FIG. 35 is a perspective view of a substrate of the implant of FIG. 31.
Figure 36:
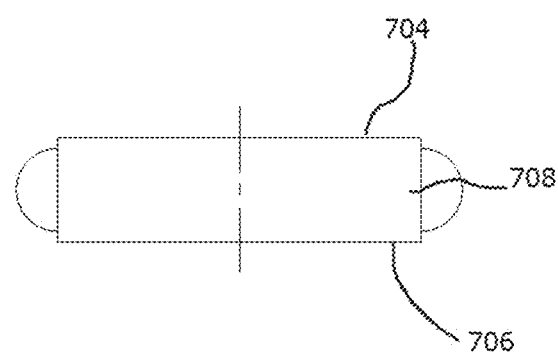
FIG. 36 is an end elevational view of the substrate in FIG. 35.
Figure 37:
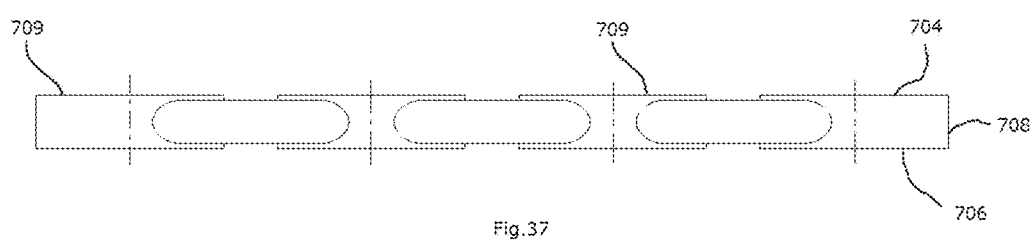
FIG. 37 is a side elevational view of the substrate of FIG. 35 31.
Figure 38:
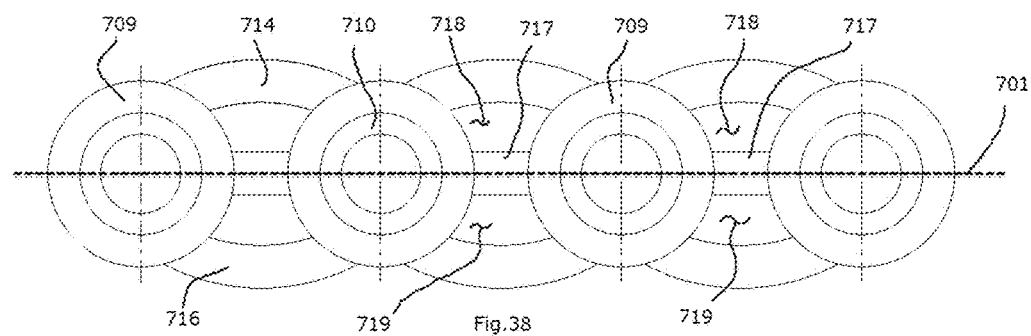
FIG. 38 is a top planar view of the substrate of FIG. 35.
Figure 39:
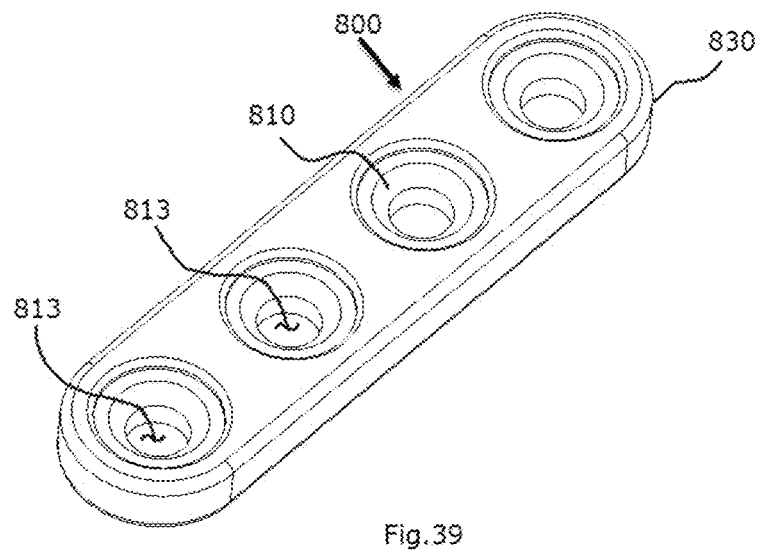
FIG. 39 is a perspective view of another alternative embodiment of an internal fixation implant of the present invention.
Figure 40:
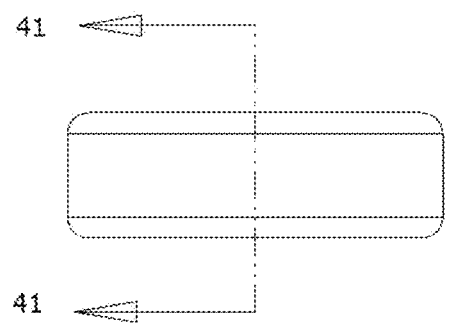
FIG. 40 is an end elevational view of the implant shown in FIG. 39.
Figure 41:
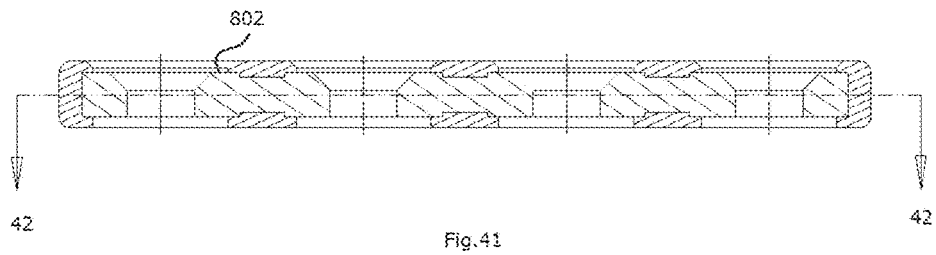
FIG. 41 is a side elevational view of the implant of FIG. 40, in section, taken along lines 41-41 of FIG. 40.
Figure 42:
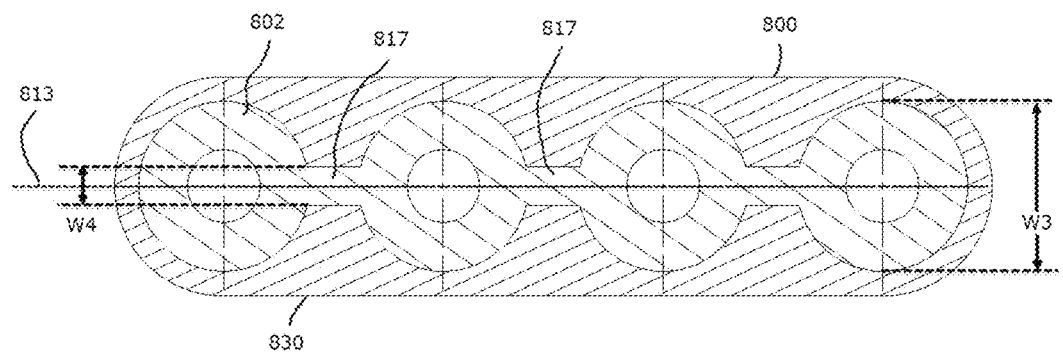
FIG. 42 is a top planar view of the implant of FIG. 41, in section, taken along lines 42-42 of FIG. 41.
Figure 43:
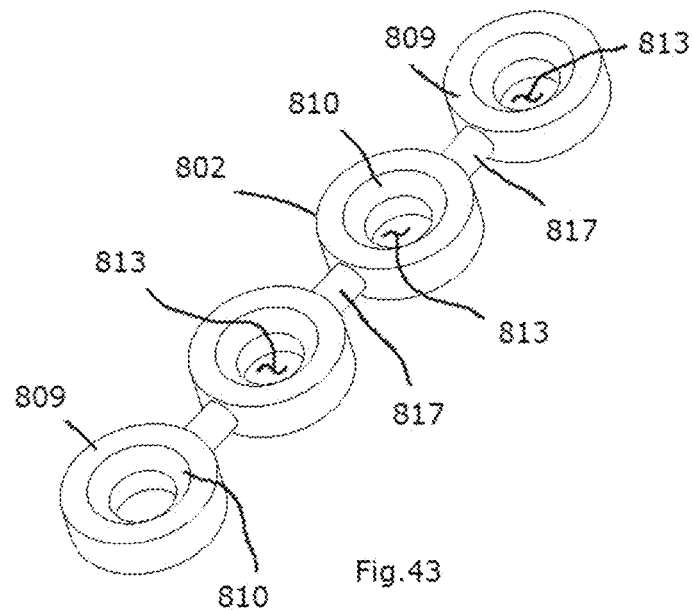
FIG. 43 is a perspective view of a substrate of the implant of FIG. 39.
Figure 44:
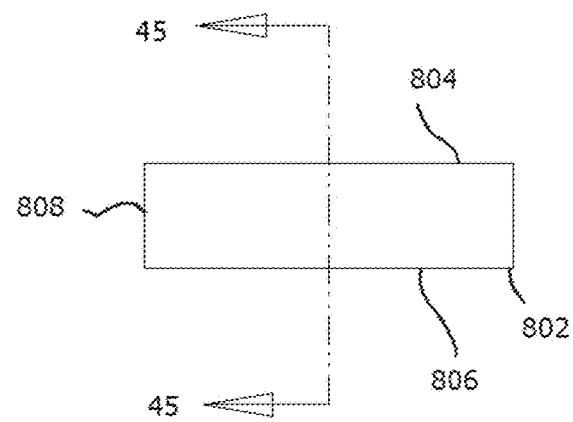
FIG. 44 is an end elevational view of the substrate shown in FIG. 43.
Figure 45:
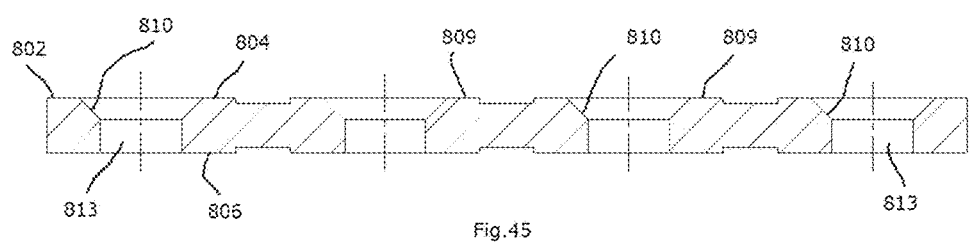
FIG. 45 is a side elevational view, in section, of the substrate of FIG. 44, taken along lines 45-45 of FIG. 44.
Figure 46:
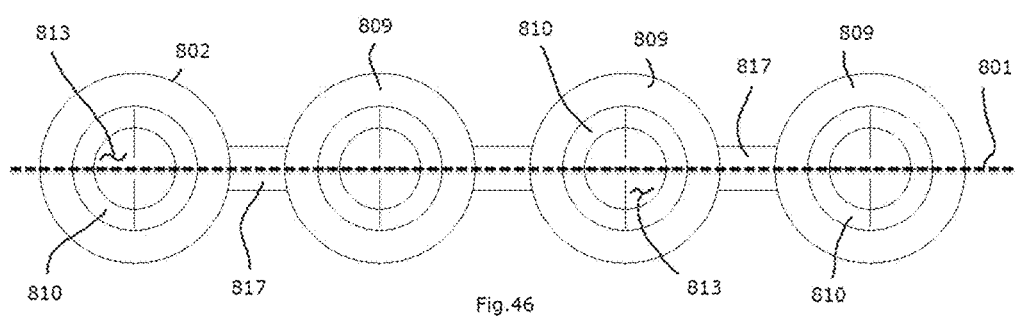
FIG. 46 is a top planar view of the substrate of FIG. 43
Figure 47:
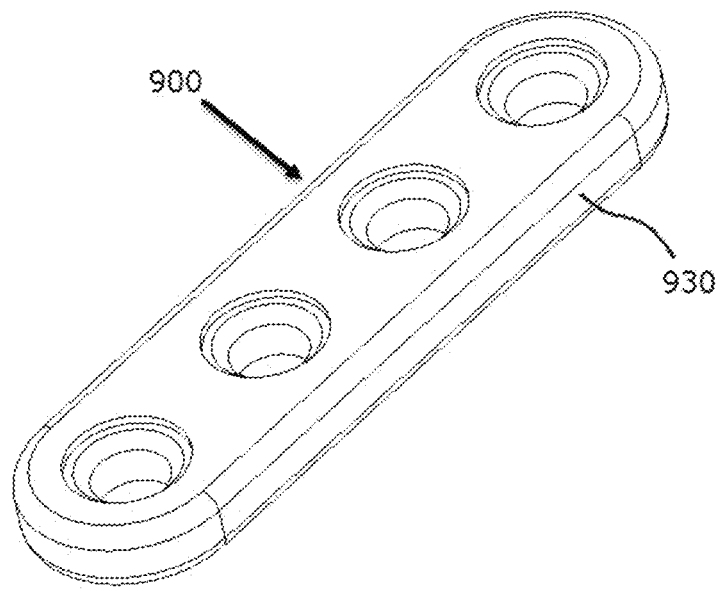
FIG. 47 is a perspective view of another alternative embodiment of an internal fixation implant of the present invention.
Figure 48:
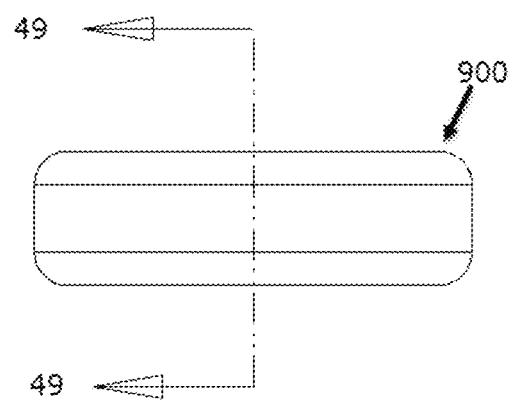
FIG. 48 is an end elevational view of the implant shown in FIG. 47.
Figure 49:
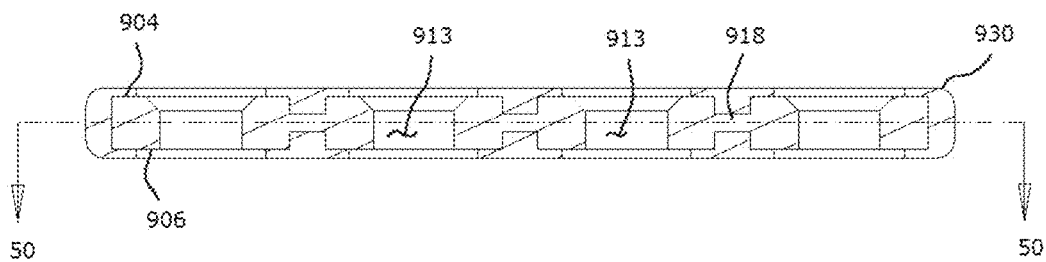
FIG. 49 is a side elevational view of the implant of FIG. 48, in section, taken along lines 49-49 of FIG. 48.
Figure 50:
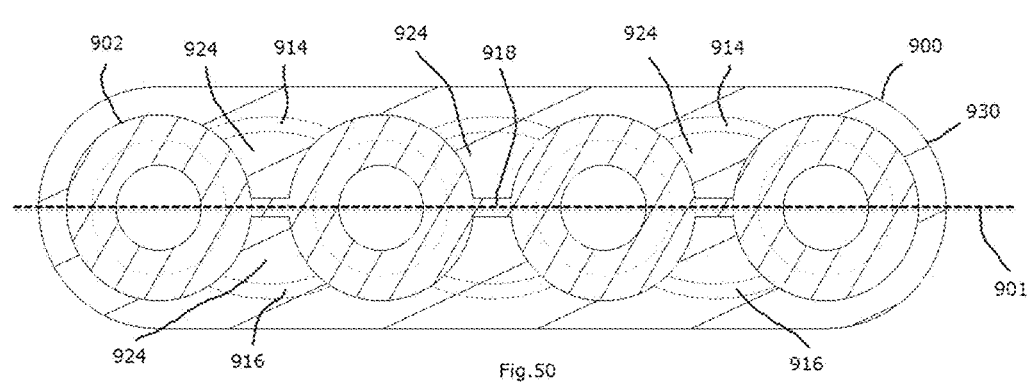
FIG. 50 is a top planar view of the implant of FIG. 49, in section, taken along lines 50-50 of FIG. 49.
Figure 51:
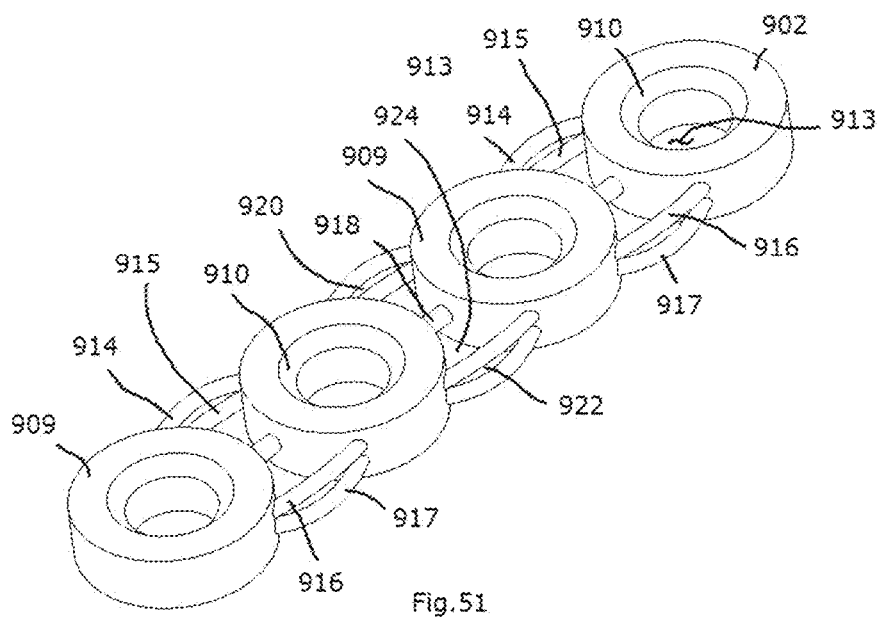
FIG. 51 is a perspective view of a substrate of the implant of FIG. 47.
Figure 52:
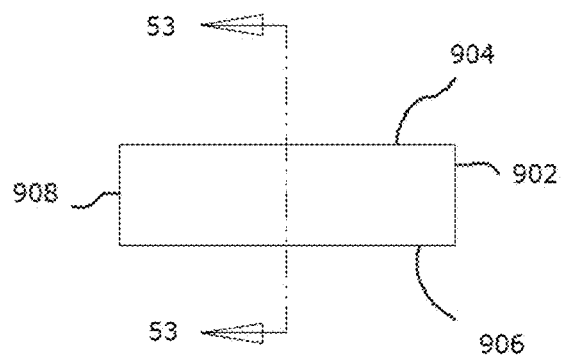
FIG. 52 is an end elevational view of the substrate shown in FIG. 51.
Figure 53:
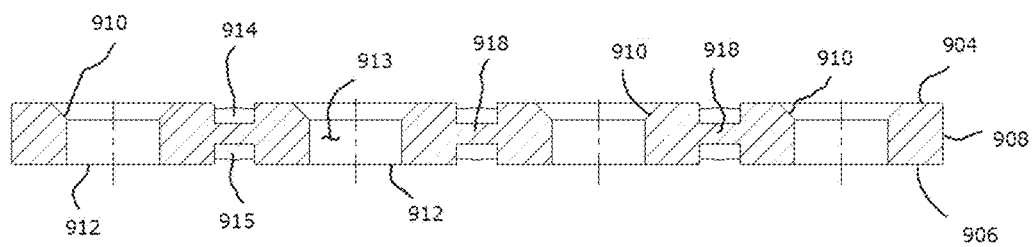
FIG. 53 is a side elevational view, in section, of the substrate of FIG. 52, taken along lines 53-53 of FIG. 52.
Figure 54:
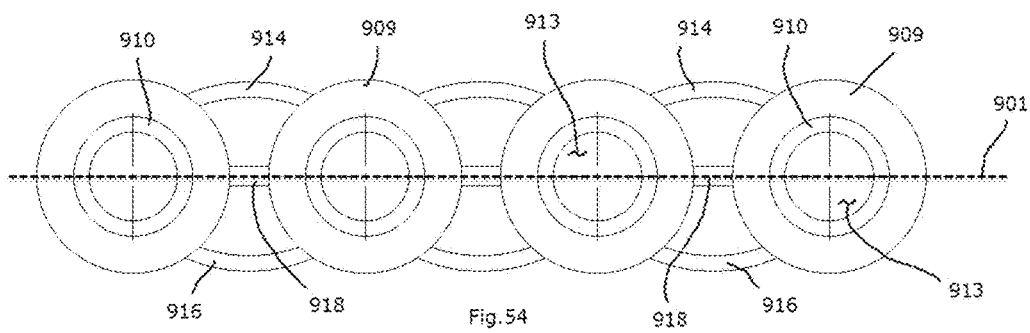
FIG. 54 is a top planar view of the substrate of FIG. 51.
Figure 55:
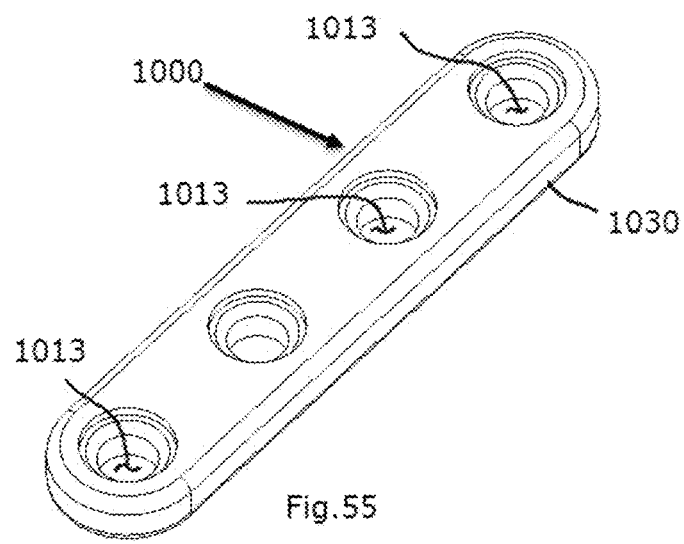
FIG. 55 is a perspective view of another alternative embodiment of an internal fixation implant of the present invention.
Figure 56:
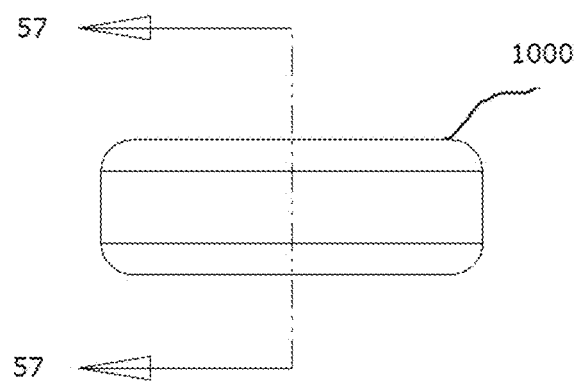
FIG. 56 is an end elevational view of the implant shown in FIG. 55.
Figure 57:
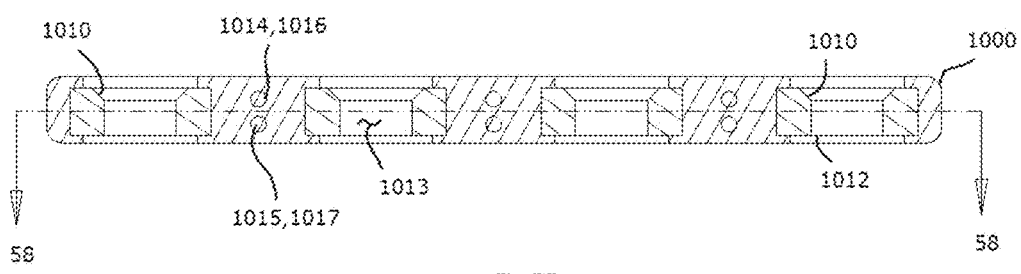
FIG. 57 is a side elevational view of the implant of FIG. 56, in section, taken along lines 57-57 of FIG. 56.
Figure 58:
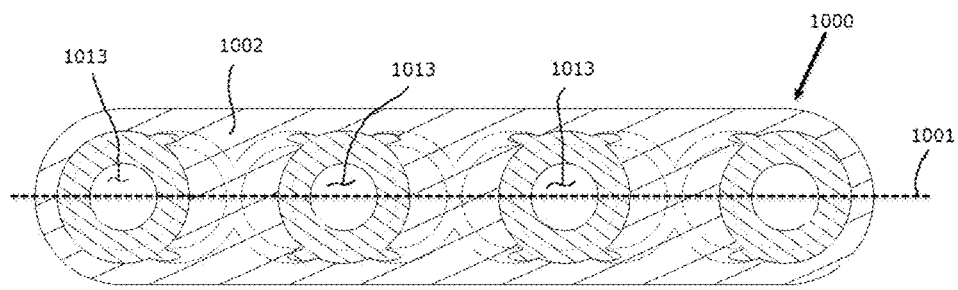
FIG. 58 is a top planar view of the implant of FIG. 57, in section, taken along lines 58-58 of FIG. 57.
Figure 59:
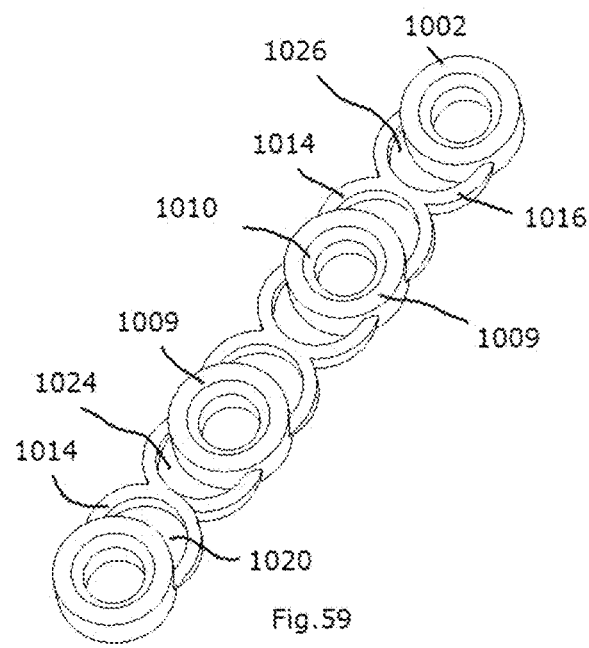
FIG. 59 is a perspective view of a substrate of the implant of FIG. 58.
Figure 60:
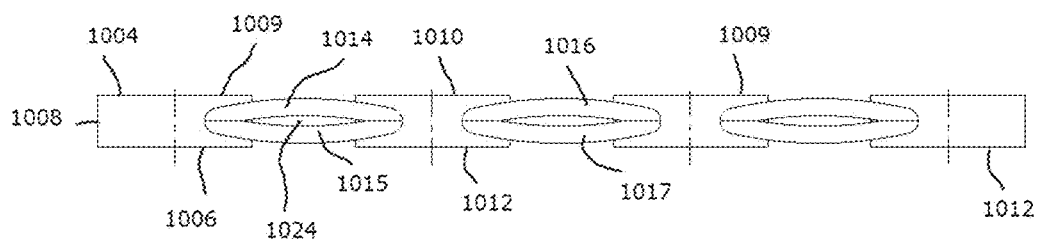
FIG. 60 is a side elevational view of the substrate of FIG. 59.
Figure 61:
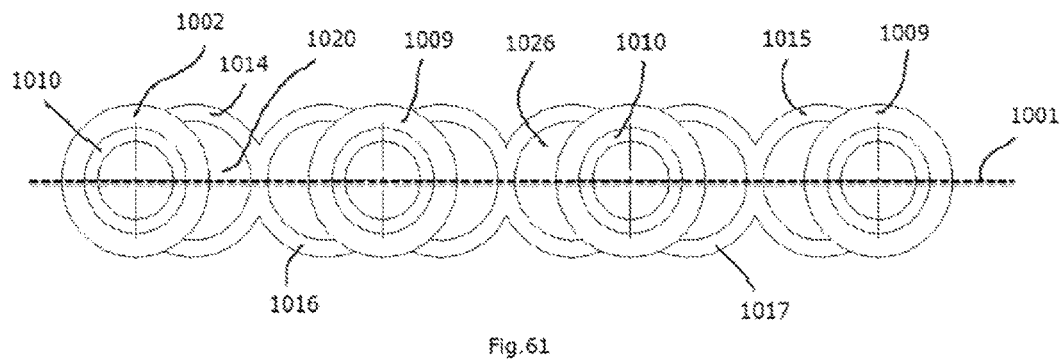
FIG. 61 is a top planar view of the substrate of FIG. 59.

Substrate 602 has a central longitudinal axis 601 and a first longitudinal side 614 extending parallel to and on a first side of longitudinal axis 601. Substrate 602 also has a second longitudinal side 616 extending parallel to and on a second side of longitudinal axis 601, distal from first longitudinal axis 601. Longitudinal sides 614, 616 connect adjacent connection portions 609 to each other. A void 618 defined by longitudinal sides 614, 616 and adjacent connection portions 609 extends through substrate 602. As shown in FIG. 30, void 618 can have a generally hourglass shape, although those skilled in the art will recognize that void 618 can have other shapes as well.

An outer covering 630 substantially encompasses substrate 602. Outer covering 630 extends around through-openings 613 and encompasses first and second longitudinal sides 614, 616. Outer covering 630 also extends into each void 618. By extending into voids 618, outer covering 630 is securely affixed to substrate 602 by vertically crossing central longitudinal axis 601.

Referring now to FIGS. 31-38, a medical implant 700 according to an alternative exemplary embodiment of the present invention is shown. Implant 700 includes a substrate 702 having a superior surface 704, an opposing inferior surface 706, and a central portion 708 between and connecting superior surface 704 and inferior surface 706.

Substrate 702 also includes plurality of discrete connection portions 709 that each has an inwardly tapered top surface 710 at superior surface 704, a bottom surface 712 at inferior surface 706, and a through-opening 713 extending between top surface 710 and bottom surface 712. Each through-opening 713 is sized to allow a connection member, such as a screw (not shown) to be inserted therethrough to secure implant 700 to a structure, such as bone.

Substrate 702 has a central longitudinal axis 701 and a first arcuate longitudinal rib 714 extending on a first side of longitudinal axis 701. Substrate 702 also has a second arcuate longitudinal rib 716 extending on a second side of longitudinal axis 701, distal from first longitudinal rib 714. Longitudinal ribs 714, 716 connect adjacent connection portions 709 to each other. An axial member 717 extends along central longitudinal axis 701 between each connection portion 709. A first void 718 defined by rib 714, axial member 717 and adjacent connection portions 709 extends through substrate 702. A second void 719 defined by rib 716, axial member 717 and adjacent connection portions 709 also extend through substrate 702.

In an exemplary embodiment, each of rib 714, 716 and axial member 717 has a generally circular cross section. Those skilled in the art, however, will recognize that the cross sections can be other shapes, such as rectangular, triangular, "I"-shaped, "T"-shaped, non-uniform cross section, or other suitable shapes.

An outer covering 730 substantially encompasses substrate 702. Outer covering 730 extends around through-openings 713 and encompasses first and second arcuate longitudinal ribs 714, 716, as well as axial member 717. Outer covering 730 also extends into each void 718, 719. By extending into voids 718, 719, outer covering 730 is securely affixed to substrate 702 around axial member 717.

First and second arcuate longitudinal ribs 714, 716, as well as axial member 717 are sufficiently thin to allow substrate 702 to be bent along any combination of axes extending orthogonal to longitudinal axis 701 between connection portions 709. Further, the arcuate nature of first and second longitudinal ribs 714, 716 results in first and second longitudinal ribs 714, 716 being longer than axial member 717, allowing substrate 702 to be torsionally twisted along longitudinal axis 701, as may be required to accommodate a particular anatomy.

Referring now to FIGS. 39-46, a medical implant 800 according to an alternative exemplary embodiment of the present invention is shown. Implant 800 includes a substrate 802 having a superior surface 804, an opposing inferior surface 806, and a central portion 808 between and connecting superior surface 804 and inferior surface 806.

Substrate 802 also includes plurality of discrete connection portions 809 that each has an inwardly tapered top surface 810 at superior surface 804, a bottom surface 812 at inferior surface 806, and a through-opening 813 extending between top surface 810 and bottom surface 812. Each through-opening 813 is sized to allow a connection member, such as a screw (not shown) to be inserted therethrough to secure implant 800 to a structure, such as bone.

Substrate 802 has a central longitudinal axis 801 and an axial member 817 extends along central longitudinal axis 801. Connection portions 809 have a first width W3 and axial members 817 have a second width W4, different from the first width W3. In an exemplary embodiment, second width W4 is smaller than first width W3.

In an exemplary embodiment, each axial member 817 has a generally circular cross section. Those skilled in the art, however, will recognize that the cross sections can be other shapes, such as rectangular, triangular, "I"-shaped, "T"-shaped, non-uniform cross section, or other suitable shapes.

An outer covering 830 substantially encompasses substrate 802. Outer covering 830 extends around through-openings 813 and encompasses axial member 817.

Axial member 817 is sufficiently thin to allow substrate 802 to be bent along any combination of axes extending orthogonal to longitudinal axis 801 between connection portions 809. Further, substrate 802 can be torsionally twisted along longitudinal axis 801 and axial member 817, as may be required to accommodate a particular anatomy.

Referring now to FIGS. 47-54, a medical implant 900 according to an alternative exemplary embodiment of the present invention is shown. Implant 900 includes a substrate 902 having a superior surface 904, an opposing inferior surface 906, and a central portion 908 between and connecting superior surface 904 and inferior surface 906.

Substrate 902 also includes plurality of discrete connection portions 909 that each has an inwardly tapered top surface 910 at superior surface 904, a bottom surface 912 at inferior surface 906, and a through-opening 913 extending between top surface 910 and bottom surface 912. Each through-opening 913 is sized to allow a connection member, such as a screw (not shown) to be inserted therethrough to secure implant 900 to a structure, such as bone.

Substrate 902 has a central longitudinal axis 901 and a plurality of arcuate longitudinal ribs 914, 915 extending on a first side of longitudinal axis 901. Substrate 902 also has a plurality of second arcuate longitudinal ribs 916, 917 extending on a second side of longitudinal axis 901, distal from first longitudinal ribs 914, 915. Longitudinal ribs 914, 915, 916, 917 connect adjacent connection portions 909 to each other at central portion 908. Each longitudinal rib 914, 915, 916, 917 can extend in a plane that is generally oblique with respect to a central horizontal plane extending through central portion 908. An axial member 918 extends along central longitudinal axis 901 and connects adjacent connection portions 909.

In an exemplary embodiment, each of rib 914, 915, 916, 917 has a generally circular cross section. Those skilled in the art, however, will recognize that the cross sections can be other shapes, such as rectangular, triangular, "I"-shaped, "T"-shaped, non-uniform cross section, or other suitable shapes.

A void 920 is formed between rib 914 and rib 915; a void 922 is formed between rib 916 and rib 917; and a void 924 is formed between ribs 914, 915 and ribs 916, 917.

An outer covering 930 substantially encompasses substrate 902. Outer covering 930 extends around through-openings 913 and encompasses longitudinal ribs 914, 915, 916, 917 and axial member 918. Outer covering 930 also extends into each void 920, 922, 924. By extending into voids 920, 922, 924, outer covering 930 is securely affixed to substrate 902 around longitudinal ribs 914, 915, 916, 917 and axial member 918.

Longitudinal ribs 914, 915, 916, 917 are sufficiently thin to allow substrate 902 to be bent along any combination of axes extending orthogonal to longitudinal axis 901 between connection portions 909. Further, the arcuate nature of longitudinal ribs 914, 915, 916, 917 allows substrate 902 to be torsionally twisted along longitudinal axis 901, as may be required to accommodate a particular anatomy.

Referring now to FIGS. 55-61, a medical implant 1000 according to an alternative exemplary embodiment of the present invention is shown. Implant 1000 includes a substrate 1002 having a superior surface 1004, an opposing inferior surface 1006, and a central portion 1008 between and connecting superior surface 1004 and inferior surface 1006.

Substrate 1002 also includes plurality of discrete connection portions 1009 that each has an inwardly tapered top surface 1010 at superior surface 1004, a bottom surface 1012 at inferior surface 1006, and a through-opening 1013 extending between top surface 1010 and bottom surface 1012. Each through-opening 1013 is sized to allow a connection member, such as a screw (not shown) to be inserted therethrough to secure implant 1000 to a structure, such as bone.

Substrate 1002 has a central longitudinal axis 1001 and a plurality of first arcuate ribs 1014, 1015 extending from a connecting portion 1009 on a first side of longitudinal axis 901, across longitudinal axis 901, and back to connecting portion 1009 in an arcuate manner. Substrate 1002 also has a plurality of second arcuate ribs 1016, 1017 extending from an adjacent connecting portion 1009 on the first side of longitudinal axis 1001, across longitudinal axis 1001, and back to connecting portion 1009 in an arcuate manner. Rib 1014 connects to rib 1016 at their respective apices and rib 1015 connects to rib 1017 at their respective apices. Each rib 1014, 1015, 1016, 1017 can extend in a plane that is generally oblique with respect to a central horizontal plane extending through central portion 1008.

In an exemplary embodiment, each of rib 1014, 1015, 1016, 1017 has a generally circular cross section. Those skilled in the art, however, will recognize that the cross sections can be other shapes, such as rectangular, triangular, "I"-shaped, "T"-shaped, non-uniform cross section, or other suitable shapes.

A void 1020 is formed between connecting portion 1009 and ribs 1014, 1015; a void 1022 is formed connecting portion 1009 and ribs 1016, 1017; a void 1024 is formed between rib 1014 and rib 1015; and a void 1026 is formed between rib 1016 and rib 1017.

An outer covering 1030 substantially encompasses substrate 1002. Outer covering 1030 extends around through-openings 1013 and encompasses ribs 1014, 1015, 1016, 1017. Outer covering 1030 also extends into each void 1020, 1022, 1024, 1026. By extending into voids 1020, 1022, 1024, 1026, outer covering 1030 is securedly affixed to substrate 1002 around ribs 1014, 1015, 1016, 1017.

Ribs 1014, 1015, 1016, 1017 are sufficiently thin to allow substrate 1002 to be bent along any combination of axes extending orthogonal to longitudinal axis 1001 between connection portions 1009. Further, the arcuate nature of ribs 1014, 1015, 1016, 1017 allows substrate 1002 to be torsionally twisted along longitudinal axis 1001, as may be required to accommodate a particular anatomy.

Figure 62:
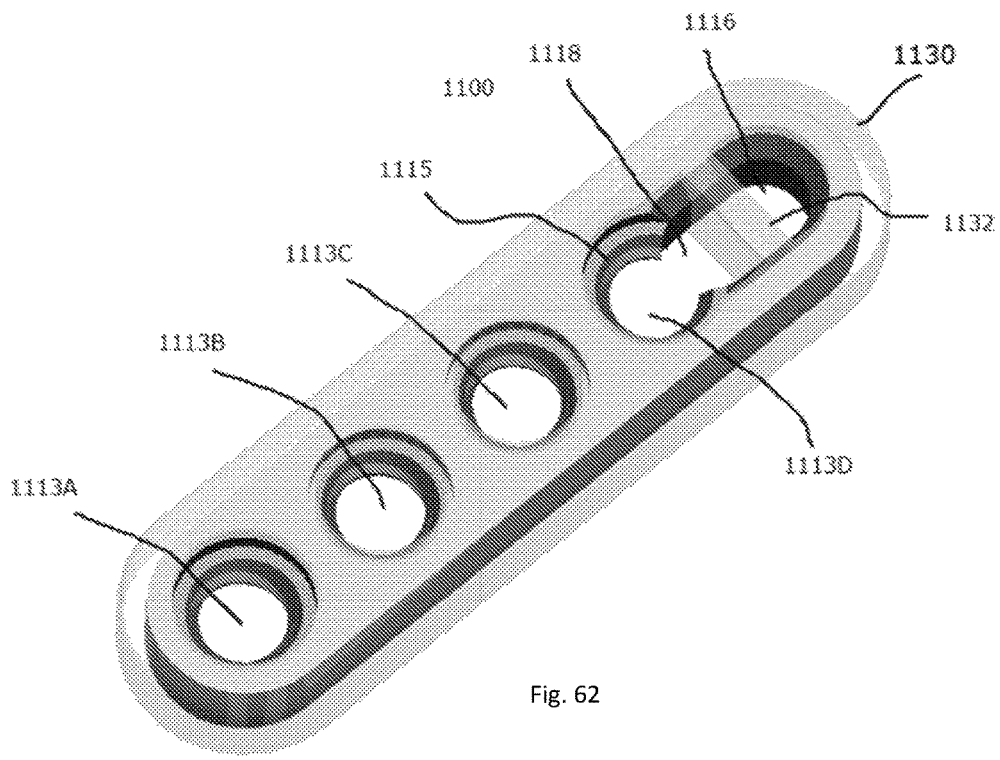
FIG. 62 is a perspective view of another alternative embodiment of an internal fixation implant of the present invention.
Figure 63:
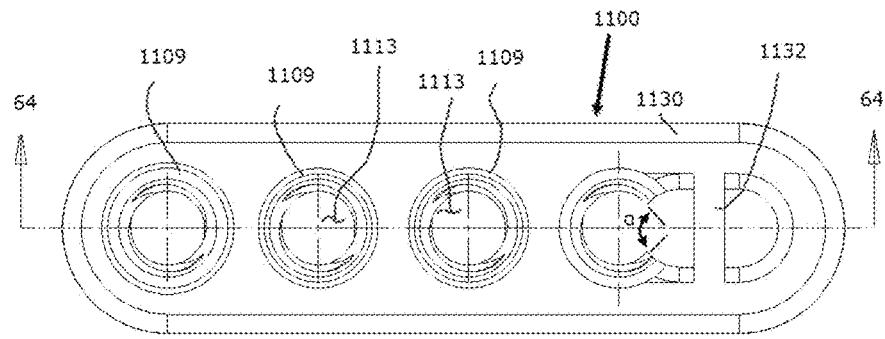
FIG. 63 is a top plan view of the implant of FIG. 62.
Figure 64:
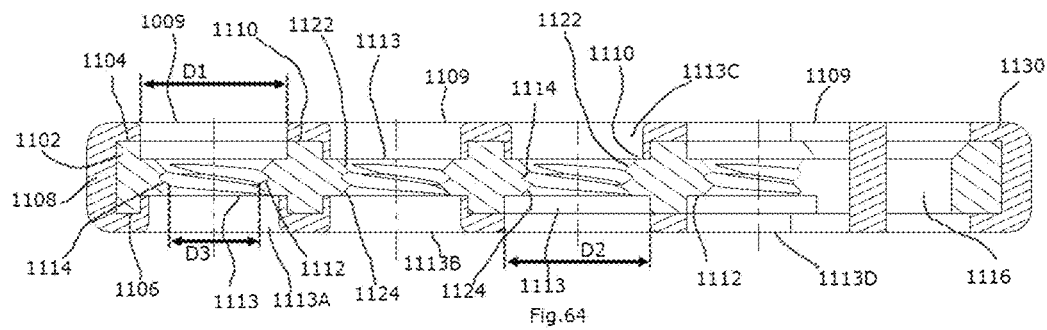
FIG. 64 is a side elevational view, in section, of the implant of FIG. 63, taken along lines 64-64 of FIG. 63.

Referring now to FIGS. 62-64, a medical implant 1100 according to an alternative exemplary embodiment of the present invention is shown. Implant 1100 includes a substrate 1102 having a superior surface 1104, an opposing inferior surface 1106, and a central portion 1108 between and connecting superior surface 1104 and inferior surface 1106.

Substrate 1102 also includes plurality of discrete connection portions 1109 that each has a top surface 1110, a bottom surface 1112, and a through-opening 1113 extending between top surface 1110 and bottom surface 1112. Each through-opening 1113 is sized to allow a connection member, such as a screw (not shown) to be inserted therethrough to secure implant 1100 to a structure, such as bone.

Through-opening 1113 is shown in detail in FIG. 64 and can be threaded or non-threaded. Through-opening 1113 has a first diameter D1 proximate to top surface 1110 and a second diameter D2 proximate to bottom surface 1112. In an exemplary embodiment, diameter D1 and D2 are the same. A central portion 1114, between first diameter D1 and second diameter D2 has a third diameter D3, smaller than diameters D1 and D2. Central portion 1114 has a superior chamfered edge 1122 and an inferior chamfered edge 1124. Central portion 1114 extends contiguously 360 degrees around through-opening 1113.

In an exemplary embodiment, an outer covering 1130 substantially encompasses substrate 1102. Outer covering 1130 extends around through-openings 1113 and at least a portion of outer covering 1130 extends into through-opening 1113, as shown with respect to through-openings 1113A-1113C. Regarding through-opening 1113A, outer covering 1130 extends to bottom surface 1112 of connection portion 1109. Regarding through-opening 1113B, outer covering 1130 extends to both top surface 1110 and bottom surface 1112 of connection portion 1109. Regarding through-opening 1113C, outer covering 1130 only extends to top surface 1110 of connection portion 1109.

A through-opening 1113D includes an arcuate portion 1115 that extends in an arc α of less than 360 degrees. In an exemplary embodiment, arc α is about 300 degrees, with an opening 1116 of about 60 degrees. Arcuate portion 1113 can have the same configuration as any of through-openings 1113A-C.

Through-opening 1113D further includes an oblong portion 1118 having an open end 1120 in communication with opening 1116 in arcuate portion 1113. Oblong portion 1118 is unthreaded, with a reduced inner diameter portion 1120. Portion 1120 includes a chamfered superior surface 1122 connected to a vertical side wall 1124. An annular inferior surface 1126 is connected to a bottom end of side wall 1124. Through-opening 1113D is a combined fastener hole that can accept a locking screw (not shown) in arcuate portion 1115 and/or a non-locking fastener (not shown) in oblong portion 1118.

A portion 1132 of outer covering 1130 extends into oblong portion 1118. As shown in FIG. 63, portion 1132 can be a laterally extending portion that generally bisects oblong portion 1118. Those skilled in the art, however, will recognize that portion 1132 can be different shapes and be located in different places along oblong portion 1132. In an exemplary embodiment, portion 1132 extends between top surface 1110 and bottom surface 1112.

Figure 65:
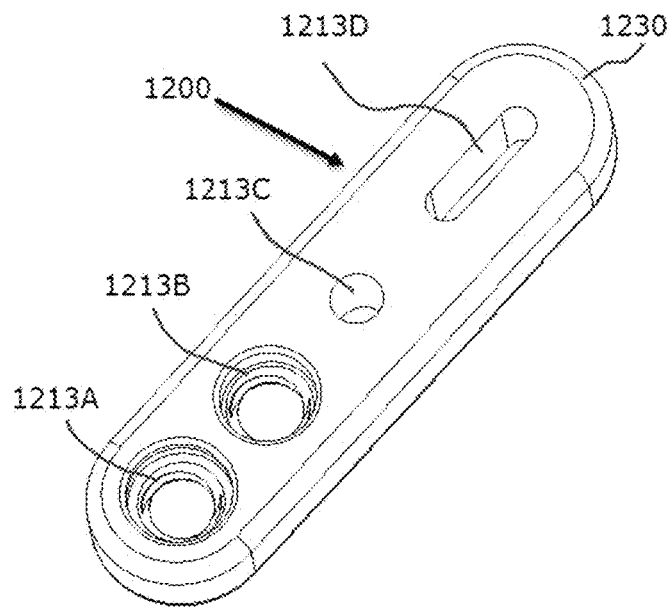
FIG. 65 is a perspective view of another alternative embodiment of an internal fixation implant of the present invention.
Figure 66:
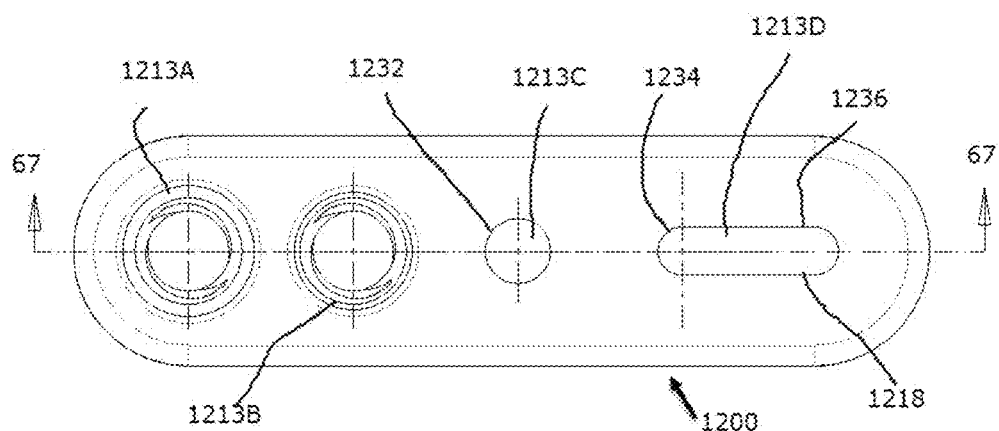
FIG. 66 is a top plan view of the implant of FIG. 65.
Figure 67:
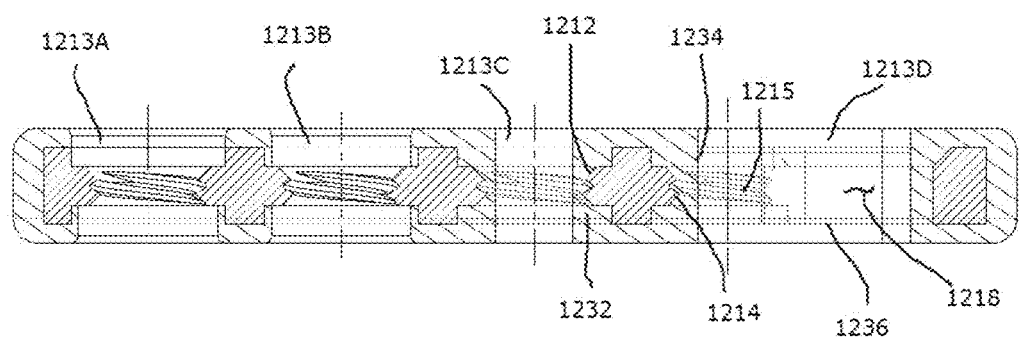
FIG. 67 is a side elevational view, in section, of the implant of FIG. 66, taken along lines 67-67 of FIG. 66.

Referring now to FIGS. 65-67, a medical implant 1200 according to an alternative exemplary embodiment of the present invention is shown. Implant 1200 includes a substrate 1202 that can be similar to substrate 1102 described above.

An outer covering 1230 substantially encompasses substrate 1202. Outer covering 1230 extends around through-openings 1213 and can extend into through-openings 1213A-1213D as described above with respect to through-openings 1113A-1113B. With regard to through-opening 1213C, a portion 1232 of outer covering 1130 extends radially into through-opening 1213C such that threads 1212 are covered by portion 1232. Through-opening 1213C, however, still allow for the insertion of a securing member (not shown) to be inserted fully therethrough. Portion 1232 allows the securing member to "bite" into portion 1232, providing a secure connection of the securing member within through-opening 1213C.

Similar to through-opening 1213C, a portion 1234 of outer covering 1230 extends into through-opening 1213D such that threads 1214 in arcuate portion 1215 are covered by portion 1234. Additionally, oblong portion 1218 is also covered by a portion 1236 of outer covering 1230 such that outer covering 1230 covers the sidewalls of oblong portion 1218 and the entirety of through-opening 1213D, leaving a narrow through passage surrounded by outer covering 1230.

Figure 68:
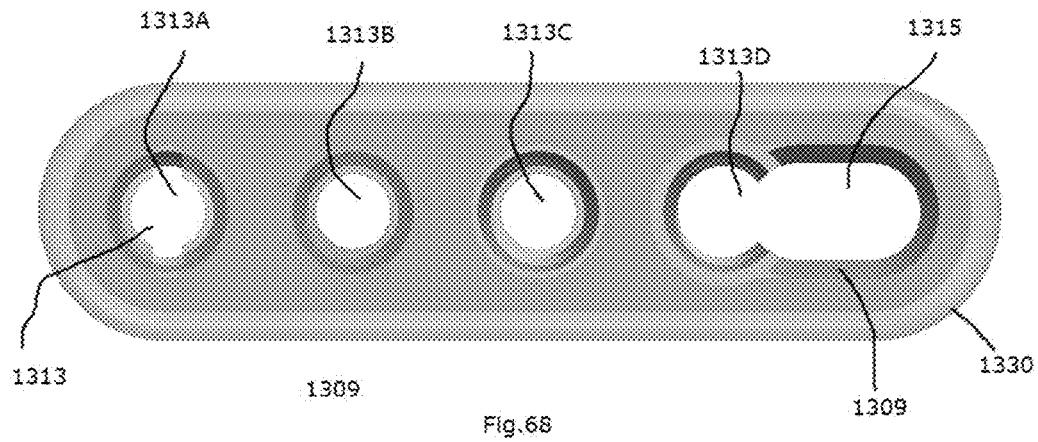
FIG. 68 is a top plan view of another alternative embodiment of an internal fixation implant of the present invention.
Figure 69:
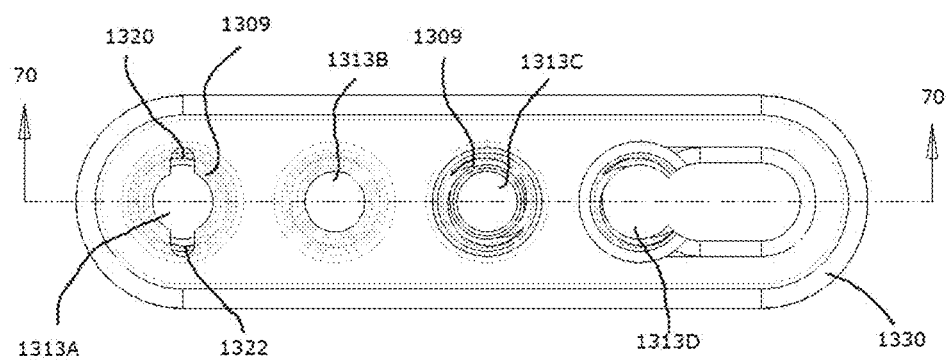
FIG. 69 is a top plan view of the implant of FIG. 68, showing substrate below the outer covering.
Figure 70:
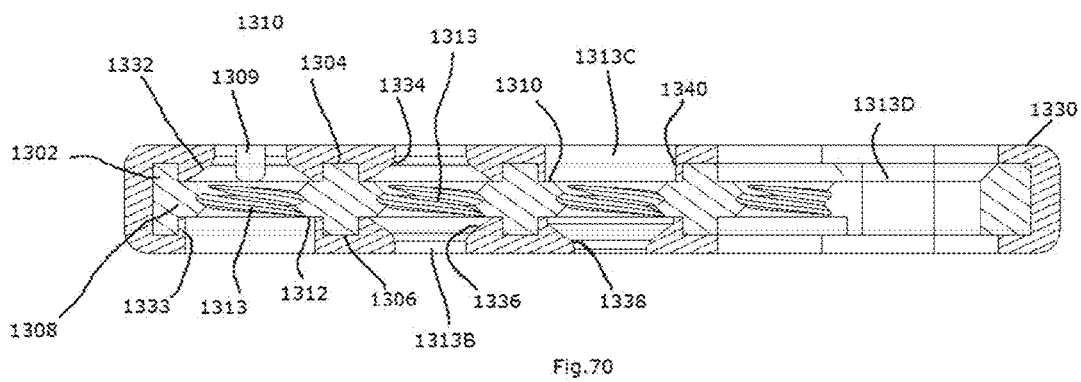
FIG. 70 is a side elevational view, in section, of the implant of FIG. 69, taken along lines 42-42 of FIG. 69.
Figure 71:
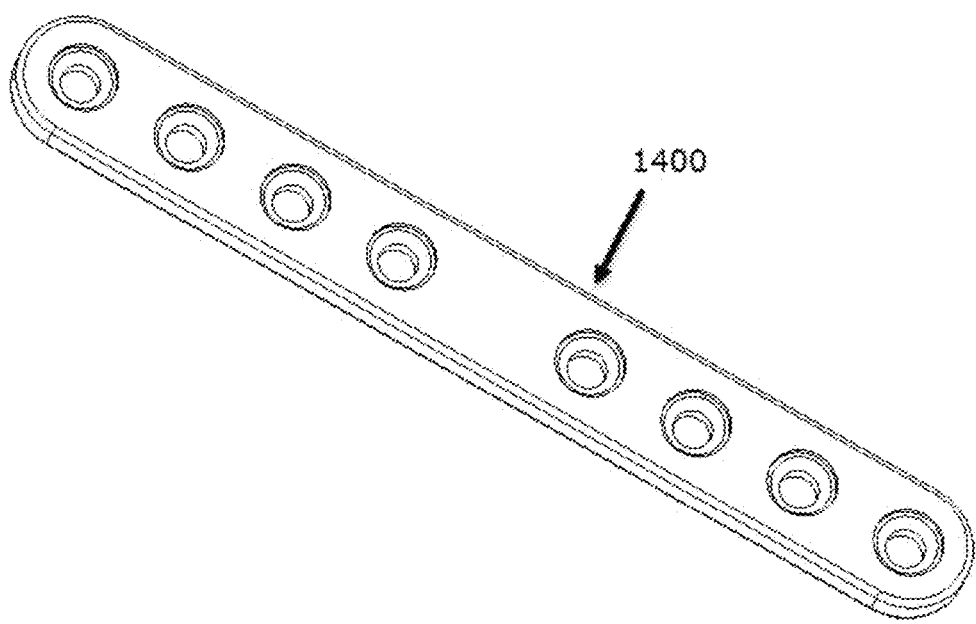
FIG. 71 is a perspective view of another alternative embodiment of an internal fixation implant of the present invention.
Figure 72:
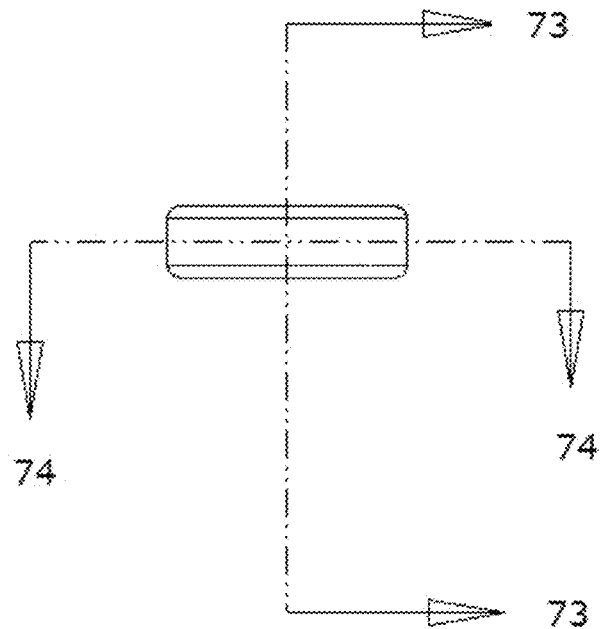
FIG. 72 is an end elevational view of the implant of FIG. 71.
Figure 73:
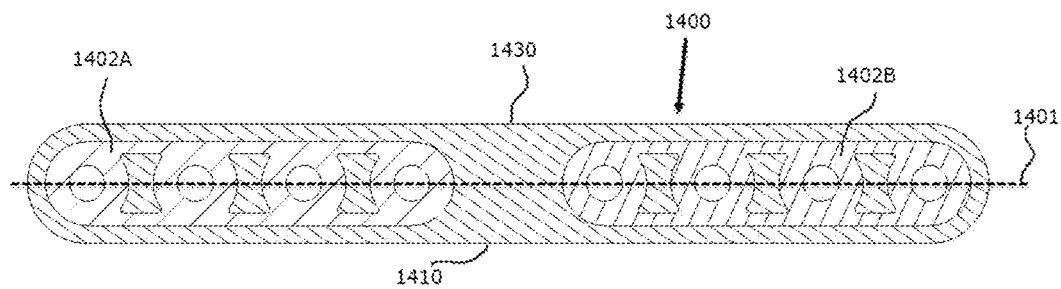
FIG. 73 is a top plan view, in section, of the implant of FIG. 72, taken along lines 73-73 of FIG. 72.
Figure 74:
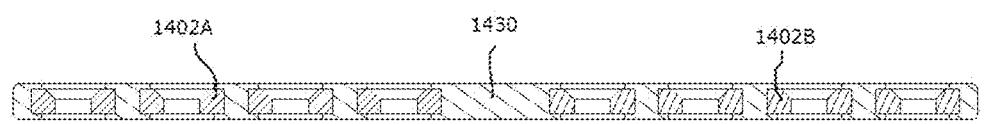
FIG. 74 is a side elevational view, in section, of the implant of FIG. 72, taken along lines 74-74 of FIG. 72.
Figure 75:
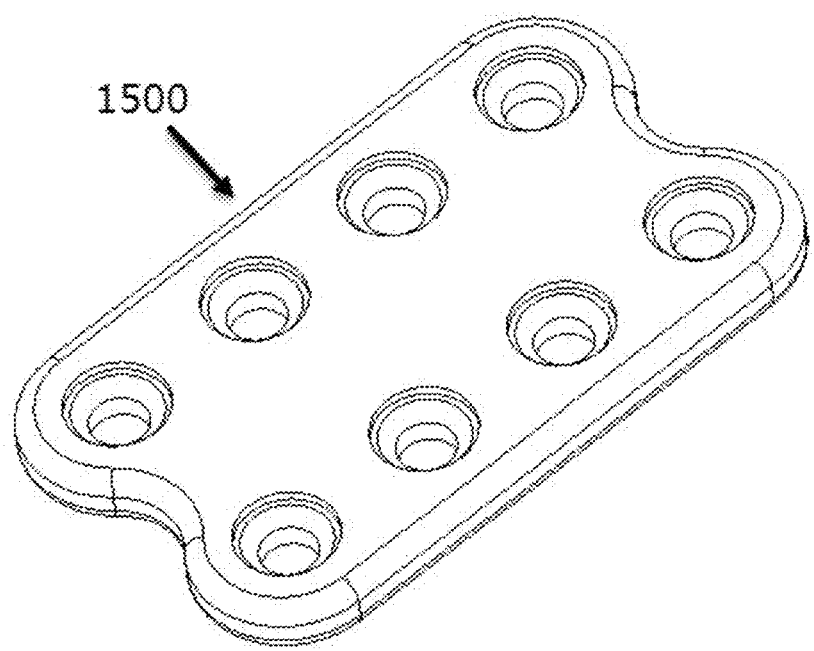
FIG. 75 is a perspective view of another alternative embodiment of an internal fixation implant of the present invention.
Figure 76:
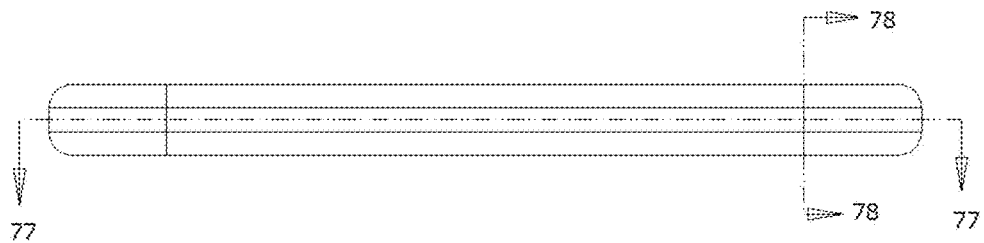
FIG. 76 is a side elevational view of the implant of FIG. 75.
Figure 77:
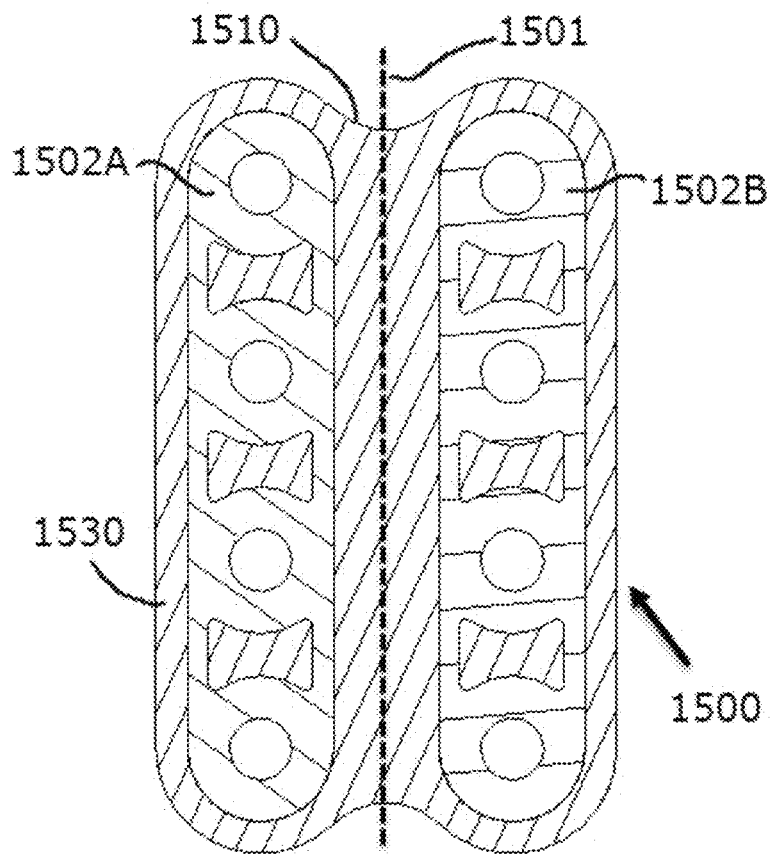
FIG. 77 is a top plan view, in section, of the implant of FIG. 76, taken along lines 77-77 of FIG. 76.
Figure 78:
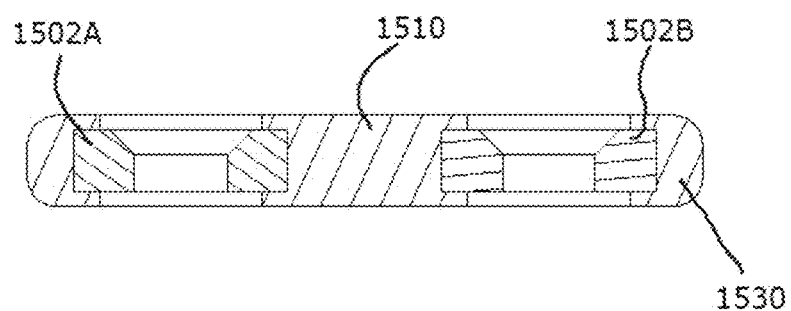
FIG. 78 is an end elevational view, in section, of the implant of FIG. 76, taken along lines 78-78 of FIG. 76.
Figure 79:
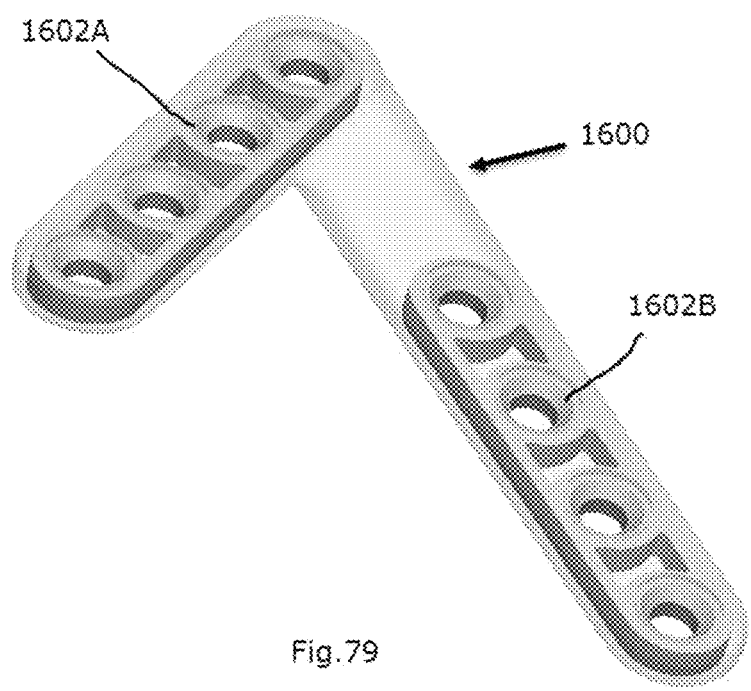
FIG. 79 is a perspective view of another alternative embodiment of an internal fixation implant of the present invention.

Referring now to FIGS. 68-70, a medical implant 1300 according to an alternative exemplary embodiment of the present invention is shown. Implant 1300 includes a substrate 1302 having a superior surface 1304, an opposing inferior surface 1306, and a central portion 1308 between and connecting superior surface 1304 and inferior surface 1306.

Substrate 1302 also includes plurality of discrete connection portions 1309 that each has a top surface 1310 proximate to superior surface 1304, a bottom surface 1312 proximate to inferior surface 1306, and a through-opening 1313 extending between top surface 1310 and bottom surface 1312. Each through-opening 1313A-D is sized to allow a connection member, such as a screw (not shown) to be inserted therethrough to secure implant 1300 to a structure, such as bone. Through-openings 1313A-D can be similar to through-openings 1213A-D described above.

An outer covering 1330 substantially encompasses substrate 1302. Outer covering 1330 extends around through-openings 1313 and can extend into through-openings 1313A-1313C as described herein.

Through-opening 1313A includes a portion 1332 of outer covering 1330 extending partially radially across through-opening 1313A, but tapering outwardly toward top surface 1310 of through-opening 1313A. As shown in FIG. 69, lobes 1320, 1322 have an absence of outer covering 1330 such that portion 1332 is not present. A portion 1333 of outer covering 1330 extends into through-opening 1313A to bottom surface 1312.

Through-opening 1313B includes a portion 1334 of outer covering 1330 extending partially radially across through-opening 1313B, but tapering outwardly toward top surface 1310 of through-opening 1313B. Similarly, a portion 1336 of outer covering 1330 extends partially radially across the bottom of through-opening 1313B, but tapers outwardly toward bottom surface 1312 of through-opening 1313B.

Through-opening 1313C includes a portion 1338 of outer covering 1330 extending partially radially across the bottom of through-opening 1313C, but tapering outwardly toward bottom surface 1312 of through-opening 1313C. A portion 1340 of outer covering 1330 extends into through-opening 1313A to top surface 1310.

Through-opening 1313D includes an arcuate portion 1315 and an oblong portion 1318 similar to through-opening 1113D. Through-opening 1313D is devoid of any outer covering extending thereinto.

Referring now to FIGS. 71-74, a medical implant 1400 according to an alternative exemplary embodiment of the present invention is shown. Implant 1400 can include any of implants 100-1300 described above, or any combination thereof. Implant 1400 includes a plurality of separate substrates 102, 402-1302 (referred to herein as substrates 1402A, 1402B) connected to each other by an outer covering 1430. Substrates 1402A, 1402B extend co-linearly along a longitudinal axis 1401 and are separated from each other by a distance 1410 where no substrate is provided.

Outer covering 1430 can have a first thickness along either or both axes that are orthogonal to longitudinal axis 1401 at substrates 1402A, 1402B and a different thickness along either axis that is orthogonal to longitudinal axis 1401 along distance 1410. The thickness of outer covering 1430 along distance 1410 can be greater or less than the thickness along substrates 1402A, 1402B. When the thickness of outer covering 1430 along distance 1410 is less than the thickness along substrates 1402A, 1402B, outer covering 1430 along distance 1410 can be considered to be a living hinge.

Referring now to FIGS. 75-78, a medical implant 1500 according to an alternative exemplary embodiment of the present invention is shown. Implant 1500 can include any of implants 100-1300 described above, or any combination thereof. Implant 1500 includes a plurality of separate substrates 102, 402-1302 (referred to herein as substrates 1502A, 1502B) connected to each other by an outer covering 1530. Substrates 1502A, 1502B extend parallel to each other along a longitudinal axis 1501 and are separated from each other by a distance 1510 where no substrate is provided.

Outer covering 1530 can have a first thickness at substrates 1502A, 1502B and a different thickness along longitudinal axis 1501 or along an axis orthogonal to longitudinal axis 1501. The thickness of outer covering 1530 along longitudinal axis 1501 or along the axis orthogonal to longitudinal axis 1501 can be greater or less than the thickness along substrates 1502A, 1502B. When the thickness of outer covering 1530 along the axis orthogonal to longitudinal axis 1501 is less than the thickness along substrates 1502A, 1502B, outer covering 1530 along the axis orthogonal to longitudinal axis 1501 can be considered to be a living hinge.

The plurality of substrates 1502A, 1502B that make up implant 1500 can be located in different planes from each other, with outer covering 1530 between substrates 102, 402-1302 extending at an angle orthogonal to the plane of at least one of substrates 1502A, 1502B. Further, while adjacent substrates 1502A, 1502B are shown as mirror images across longitudinal axis 1501, substrates 1502A, 1502B can be longitudinally offset from each other.

Figure 80:
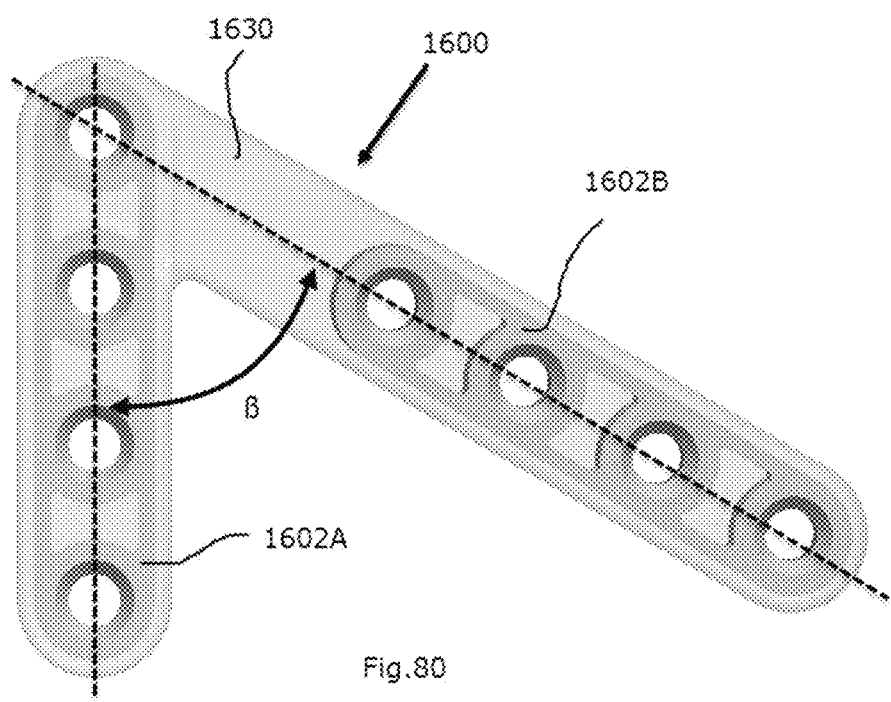
FIG. 80 is a top plan view of the implant of FIG. 79.
Figure 81:
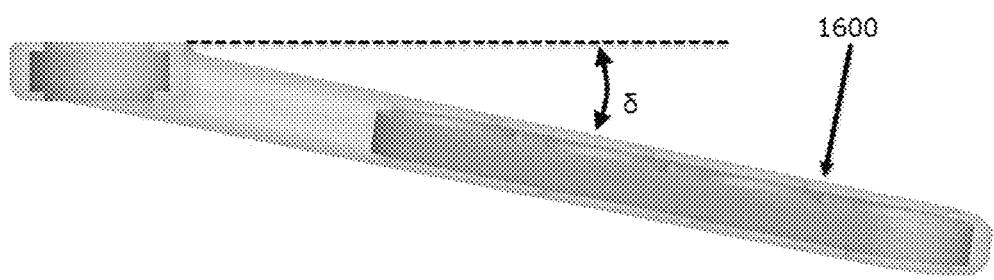
FIG. 81 is a side elevational view, of the implant of FIG. 79.
Figure 82:
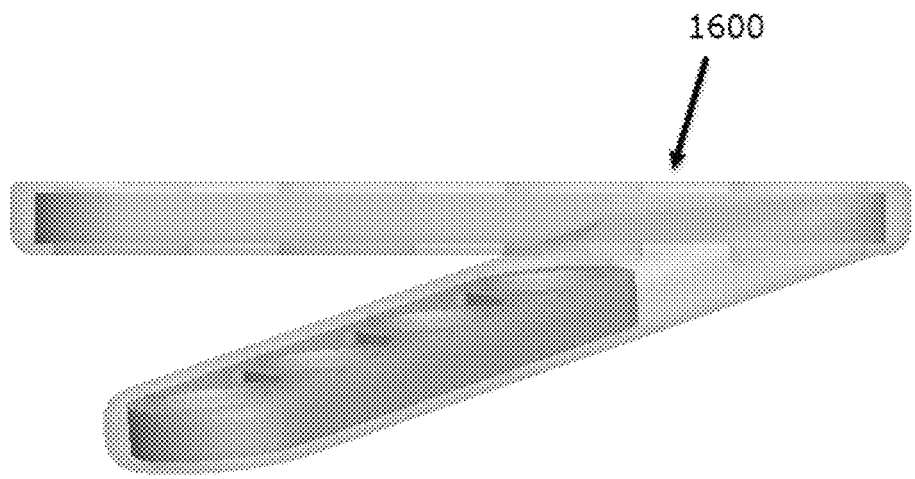
FIG. 82 is a front elevational view of the implant of FIG. 79.
Figure 83:
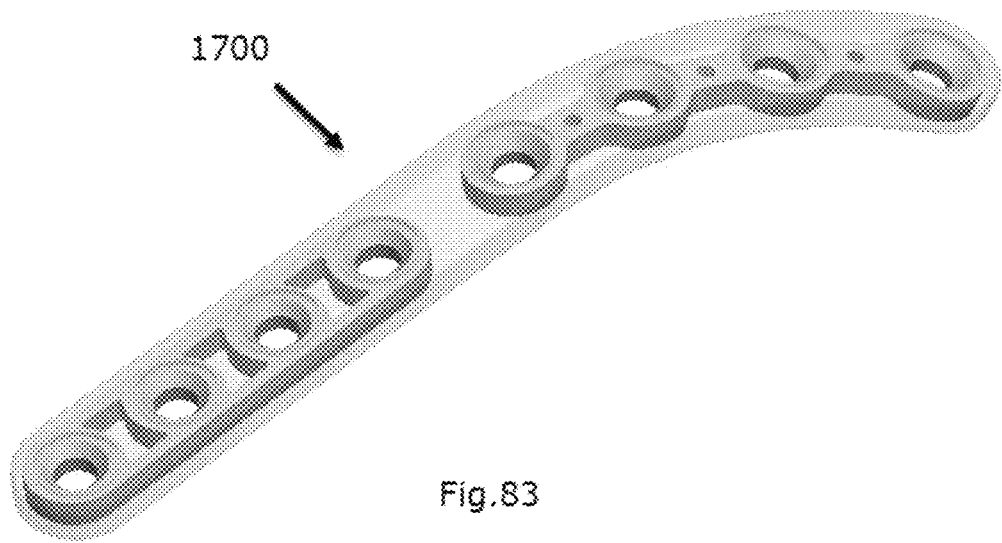
FIG. 83 is a perspective view of another alternative embodiment of an internal fixation implant of the present invention.

Referring now to FIGS. 79-82, a medical implant 1600 according to an alternative exemplary embodiment of the present invention is shown. Implant 1600 can include any of implants 100-1300 described above, or any combination thereof. Implant 1600 includes a plurality of separate substrates 102, 402-1302 (referred to herein as substrates 1602A, 1602B) connected to each other by an outer covering 1630. Substrates 1602A, 1602B can be angularly offset from each other along several planes. By way of example only, as shown in FIG. 80, substrates 1602A, 1602B can be coplanar, and offset from each other by an angle β. Alternatively, as shown in FIG. 81, substrates 1602A, 1602B can each be provided is separate planes that are angled with respect to each other by an angle δ.

While two substrates 1X02A, 1X02B are shown and described above with respect to each of implants 1400, 1500, 1600, those skilled in the art will recognize that more than two substrates can be provided.

Further, all through-openings 413-1313 described above can be configured to accept threaded or non-threaded fasteners. Through-openings 413-1313 can be different sizes, with straight, angled, beveled, curved, or flat facets within through-opening 413-1313. Shape or contour changes within through-openings 413-1313 can be smooth, abrupt, tangential, and/or contiguous.

Figure 84:
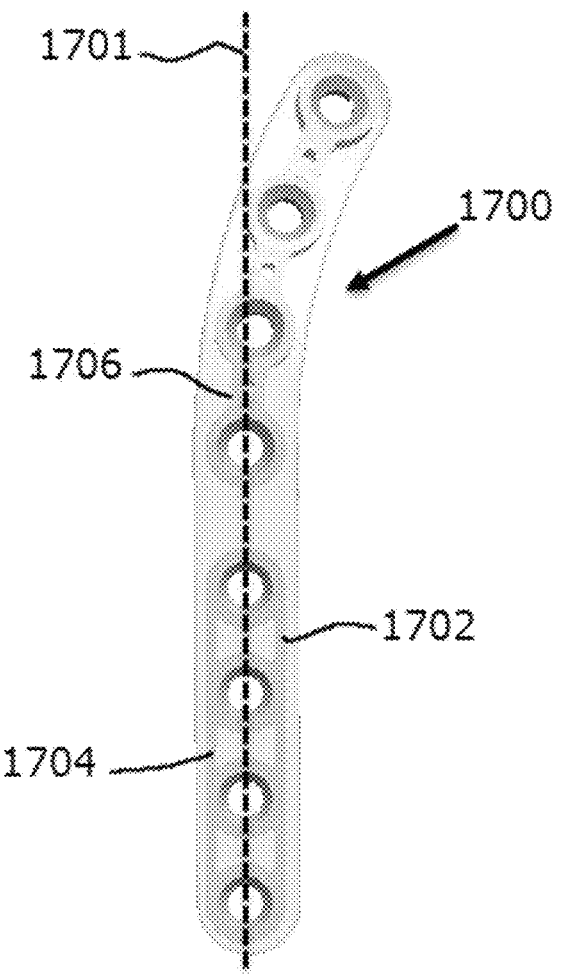
FIG. 84 is a top plan view of the implant of FIG. 83.
Figure 85:
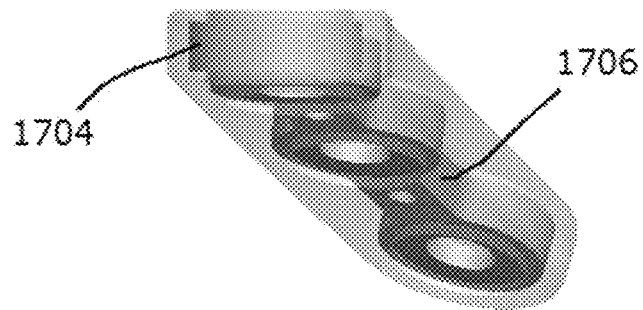
FIG. 85 is an end elevational view, of the implant of FIG. 83.
Figure 86:
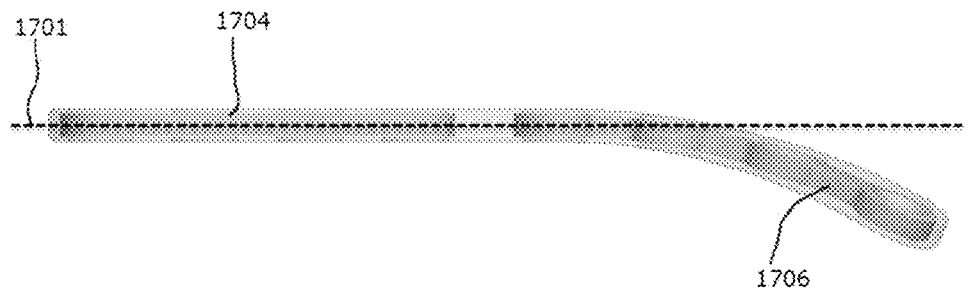
FIG. 86 is a front elevational view of the implant of FIG. 83.

Referring now to FIGS. 83-86, a medical implant 1700 according to an alternative exemplary embodiment of the present invention is shown. Implant 1700 can include any of implants 100-1300 described above, or any combination thereof. Implant 1700 includes a substrate 1702 having a generally straight substrate portion 1704 extending along a central longitudinal axis 1701 and a generally curved substrate portion 1706. As shown in FIGS. 84 and 86, curved substrate portion 1706 bends away from longitudinal axis 1701 along two orthogonal axes relative to longitudinal axis 1701, although those skilled in the art will recognize that curved substrate portion 1706 need only bend away from longitudinal axis 1701 along a single orthogonal axis relative to longitudinal axis 1701.

Figure 87:
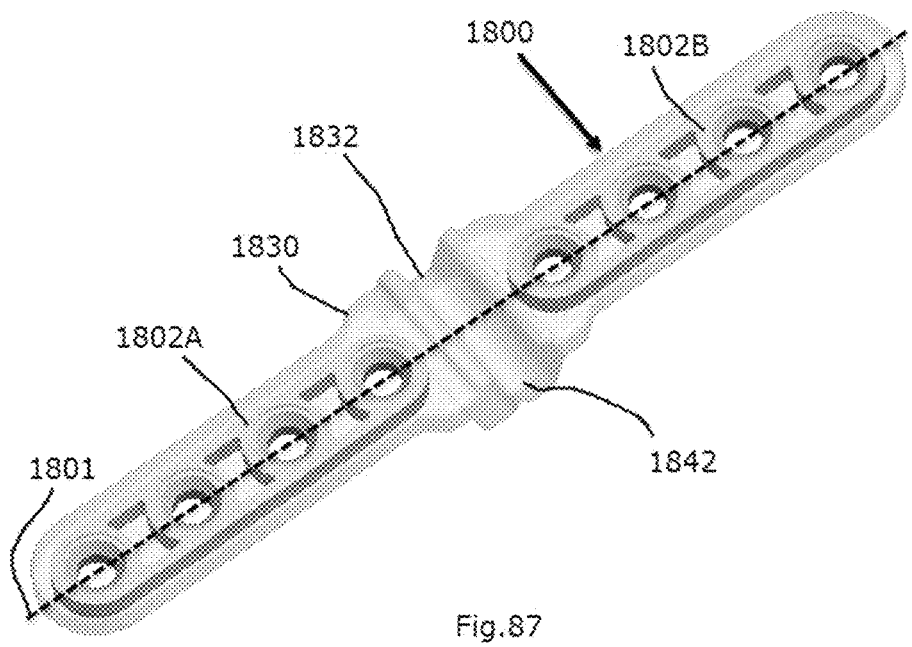
FIG. 87 is a perspective view of another alternative embodiment of an internal fixation implant of the present invention.
Figure 88:
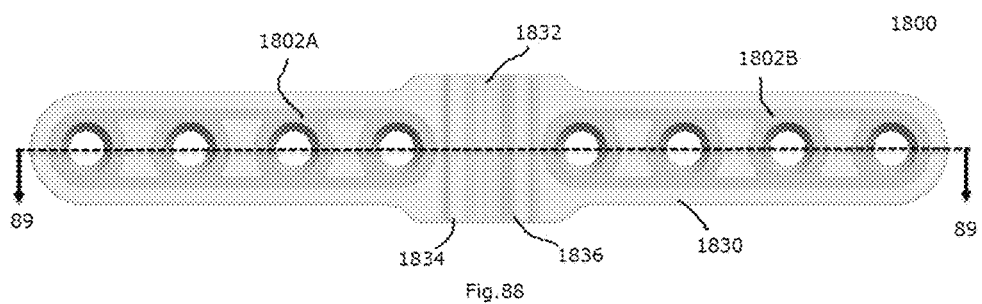
FIG. 88 is a top plan view of the implant of FIG. 87.
Figure 89:
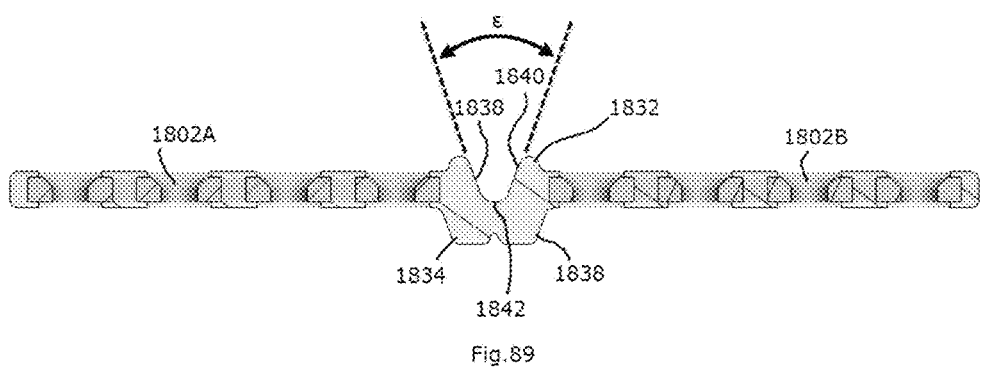
FIG. 89 is a side elevational view, in section, of the implant of FIG. 88, taken along 89-89 of FIG. 88.

Referring now to FIGS. 87-89, a medical implant 1800 according to an alternative exemplary embodiment of the present invention is shown. Implant 1800 can include any of implants 100-1300 described above, or any combination thereof. Implant 1800 includes a plurality of separate substrates 102, 402-1302 (referred to herein as substrates 1802A, 1802B) connected to each other by an outer covering 1830. Substrates 1802A, 1802B extend parallel to each other along a longitudinal axis 1801 and are separated from each other by a distance 1810 where no substrate is provided.

Outer covering 1830 can have a first thickness at substrates 1802A, 1802B. Outer covering 1830 extends between substrates 1802A, 1802B at a hinge 1832. Hinge 1832 includes a first hinge portion 1834 proximate to substrate 1802A and a second hinge portion 1836 proximate to substrate 1802B. Each of first hinge portion 1834 and second hinge portion 1836 has a face 1838, 1840, respectively, opposing the other hinge portion that is angled at an oblique angle relative to the vertical such that a combined angle ε between the faces is formed.

A hinge area 1842 is formed between faces 1838, 1840 as shown in FIG. 89. Hinge area 1842 allows implant 1800 to flex with adjacent bones, such a, for example, at a joint. Faces 1838, 1840 form a hard stop that limits the range of motion of implant to mimic a replaced or repaired joint area.

While each of the embodiments discussed above may have unique features relative to the other embodiments, those skilled in the art will recognize that a feature from one of the embodiments can be incorporated into any of the remaining embodiments and still be within the scope of this invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A medical implant comprising:
   a substrate having:
   a plurality of discrete connection portions, each connection portion having:
   a top surface;
   a bottom surface; and
   a through-opening extending between the top surface and the bottom surface; and
   a plurality of connecting members, each of the plurality of connecting members extending between two adjacent connection portions and connecting the adjacent connection portions to each other,
   wherein at least one of the plurality of connection portions has a first width and wherein at least one of the connecting members has a second width, different from the first width; and
   an elastomer outer covering substantially encompassing the substrate, the outer covering extending around but not into the through-openings such that an annular portion of the top surface of the substrate around each through-opening is exposed.

2. The medical implant according to claim 1, wherein the substrate has a central longitudinal axis, and wherein at least one of the plurality of connection portions extends along the longitudinal axis.

3. The medical implant according to claim 2, wherein the connecting member extends along the longitudinal axis.

4. The medical implant according to claim 3, wherein the connecting member comprises a plurality of additional connecting members that do not extend along the longitudinal axis.

5. The medical implant according to claim 2, wherein the connecting member does not extend along the longitudinal axis.

6. The medical implant according to claim 1, wherein at least one of the plurality of discrete connection portions is generally annularly shaped.

7. The medical implant according to claim 1, wherein the substrate further comprises a central portion between the top surface and the bottom surface, the central portion comprising a plurality of posts extending between the top surface and the bottom surface and a plurality of passages defined by each of the plurality of posts, two adjacent connection portions, and the connecting member.

8. The implant according to claim 1, further comprising a hinge formed between each of the plurality of substrates.

9. The implant according to claim 1, wherein the connecting member has an arcuate shape.

10. The implant according to claim 9, wherein the connecting member comprises a first connecting member connected to one of the connection portions and a second connecting member connected to an adjacent of the connection portions, and wherein the first connecting member and the second connecting member are connected to each other.

11. The implant according to claim 1, wherein the substrate further comprises a void between one of the connection portion and the connecting member such that the outer covering extends into the void.

12. The implant according to claim 1, wherein at least one of the through openings has a generally oblong cross section and wherein the outer covering extends through less than all of the cross section between the top surface and the bottom surface.

13. The implant according to claim 1, wherein the substrate comprises a central longitudinal axis extending therethrough and a passage extending in a central portion between the top surface and the bottom surface and having a first opening on a first side of the longitudinal axis and a second opening on the first side of the longitudinal axis.

14. The implant according to claim 1, wherein the substrate comprises a central longitudinal axis extending therethrough and a passage extending in a central portion between the top surface and the bottom surface and having a first opening on a first side of the longitudinal axis and a second opening on an opposing side of the longitudinal axis.

15. The implant according to claim 1, wherein the outer covering extends across at least a portion of one of the through-openings.

16. The implant according to claim 1, wherein the outer covering extends around the through-openings such that an annular portion of the bottom surface of the substrate around each through-opening is exposed.

17. A medical implant comprising:
a plurality of substrates, wherein each substrate comprises:
a plurality of discrete connection portions, each connection portion having:
a top surface;
a bottom surface; and
a through-opening extending between the top surface and the bottom surface; and
a plurality of connecting members, each of the plurality of connecting members extending between two adjacent connection portions and connecting the adjacent connection portions to each other,
wherein at least one of the plurality of connection portions has a first width and wherein at least one of the connecting members has a second width, different from the first width; and
an elastomer outer covering substantially encompassing the substrates, the outer covering extending around the through-openings,
wherein the implant has a first thickness at each of the substrates and second thickness, less than the first thickness, between the substrates.

18. The implant according to claim 17, wherein a first of the plurality of substrates extends in a first plane and wherein a second of the plurality of substrates extends in a second plane, different from the first plane.

* * * * *